US012562257B2

(12) United States Patent
    Gao et al.

(10) Patent No.:  US 12,562,257 B2
(45) Date of Patent:      Feb. 24, 2026

(54) SYSTEMS AND METHODS FOR MEDICAL DATA PROCESSING

(71) Applicant: SHANGHAI UNITED IMAGING METAHEALTHCARE CO., LTD., Shanghai (CN)

(72) Inventors: Jing Gao, Wuhan (CN); Ruizhi Dong, Wuhan (CN); Yuanbo Yao, Wuhan (CN); Bing Xu, Wuhan (CN); Hui Zhang, Wuhan (CN)

(73) Assignee: SHANGHAI UNITED IMAGING METAHEALTHCARE CO., LTD., Shanghai (CN)

( * ) Notice: Subject to any disclaimer, the term of this patent is extended or adjusted under 35 U.S.C. 154(b) by 467 days.

(21) Appl. No.: 18/155,710

(22) Filed: Jan. 17, 2023

(65) Prior Publication Data

US 2023/0154593 A1      May 18, 2023

Related U.S. Application Data

(63) Continuation of application No. PCT/CN2021/106971, filed on Jul. 17, 2021.

(30) Foreign Application Priority Data

| Jul. 17, 2020 | (CN) | .......................... | 202010690317.8 |
| Dec. 10, 2020 | (CN) | .......................... | 202011434314.4 |
| Dec. 17, 2020 | (CN) | .......................... | 202011495360.5 |

(51) Int. Cl.
    *G16H 30/20*        (2018.01)
    *G06T 7/00*         (2017.01)
    (Continued)

(52) U.S. Cl.
    CPC .............. *G16H 30/20* (2018.01); *G06T 7/00* (2013.01); *G16H 30/40* (2018.01); *G16H 50/20* (2018.01); *G16H 50/70* (2018.01)

(58) Field of Classification Search
    None
    See application file for complete search history.

(56) References Cited

U.S. PATENT DOCUMENTS

| 2017/0193174 A1* | 7/2017 | Allen | .................... G06F 40/279 |
| 2020/0303062 A1 | 9/2020 | Tao | |

FOREIGN PATENT DOCUMENTS

| CN | 107301241 A | 10/2017 |
| CN | 109378053 A | 2/2019 |

(Continued)

OTHER PUBLICATIONS

Machine translation of Chinese Patent Document No. 111274785, Sun et al., Jun. 12, 2020 (Year: 2020).*

(Continued)

*Primary Examiner* — Mark R Milia
(74) *Attorney, Agent, or Firm* — Poseidon Advanced IP LLC

(57) ABSTRACT

A method may include: obtaining a target image; obtaining a first feature image from the target image, the first feature image including a region of interest (ROI) in the target image; obtaining a second feature image that matches the first feature image; obtaining a knowledge graph, the knowledge graph including a relationship between the second feature image and image description information and diagnostic result information corresponding to the second feature image; obtaining the image description information and the diagnostic result information corresponding to the second feature image based on the knowledge graph and the second feature image; and generating an image report of the target image based on the target image, the image description information, and the diagnostic result information.

20 Claims, 24 Drawing Sheets

<u>100</u>

(51) Int. Cl.
   *G16H 30/40*          (2018.01)
   *G16H 50/20*          (2018.01)
   *G16H 50/70*          (2018.01)

(56)                    References Cited

FOREIGN PATENT DOCUMENTS

| | | | |
|---|---|---|---|
| CN | 109800414 | A | 5/2019 |
| CN | 110010219 | A | 7/2019 |
| CN | 110019839 | A | 7/2019 |
| CN | 110111905 | A | 8/2019 |
| CN | 110210025 | A | 9/2019 |
| CN | 110335256 | A | 10/2019 |
| CN | 110457688 | A | 11/2019 |
| CN | 110458373 | A | 11/2019 |
| CN | 110555153 | A | 12/2019 |
| CN | 110570928 | A | 12/2019 |
| CN | 110704413 | A | 1/2020 |
| CN | 110827990 | A | 2/2020 |
| CN | 110911009 | A | 3/2020 |
| CN | 111090986 | A | 5/2020 |
| CN | 111223076 | A | 6/2020 |
| CN | 111241212 | A | 6/2020 |
| CN | 111274785 | A | 6/2020 |
| CN | 111292821 | A | 6/2020 |
| CN | 111310447 | A | 6/2020 |
| CN | 111324905 | A | 6/2020 |
| CN | 111339758 | A | 6/2020 |
| CN | 111368094 | A | 7/2020 |
| CN | 111369996 | A | 7/2020 |
| CN | 111401012 | A | 7/2020 |
| CN | 111640480 | A | 9/2020 |
| CN | 111767410 | A | 10/2020 |
| CN | 111950282 | A | 11/2020 |
| CN | 111951952 | A | 11/2020 |
| CN | 112035404 | A | 12/2020 |
| CN | 112527923 | A | 3/2021 |
| CN | 112530550 | A | 3/2021 |

OTHER PUBLICATIONS

International Search Report in PCT/CN2021/106971 mailed on Sep. 15, 2021, 9 pages.

Written Opinion in PCT/CN2021/106971 mailed on Sep. 15, 2021, 9 pages.

First Office Action in Chinese Application No. 202011434314.4 mailed on Feb. 25, 2022, 27 pages.

First Office Action in Chinese Application No. 202011495360.5 mailed on Jan. 21, 2022, 13 pages.

The Extended European Search Report in European Application No. 21843125.2 mailed on Nov. 22, 2023, 11 pages.

Zhang, Yixiao et al., When Radiology Report Generation Meets Knowledge Graph, Arxiv. org, 2020, 8 pages.

* cited by examiner

100

300

400

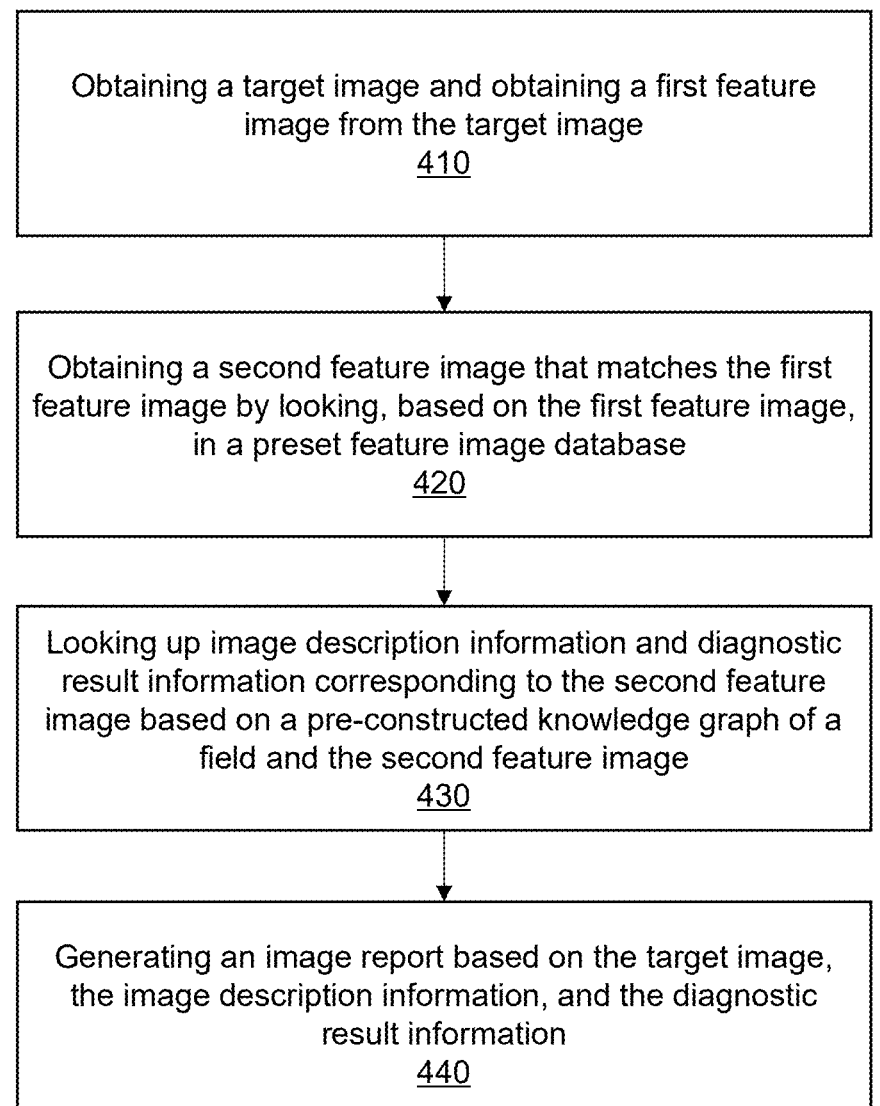

Obtaining a target image and obtaining a first feature image from the target image
410

Obtaining a second feature image that matches the first feature image by looking, based on the first feature image, in a preset feature image database
420

Looking up image description information and diagnostic result information corresponding to the second feature image based on a pre-constructed knowledge graph of a field and the second feature image
430

Generating an image report based on the target image, the image description information, and the diagnostic result information
440

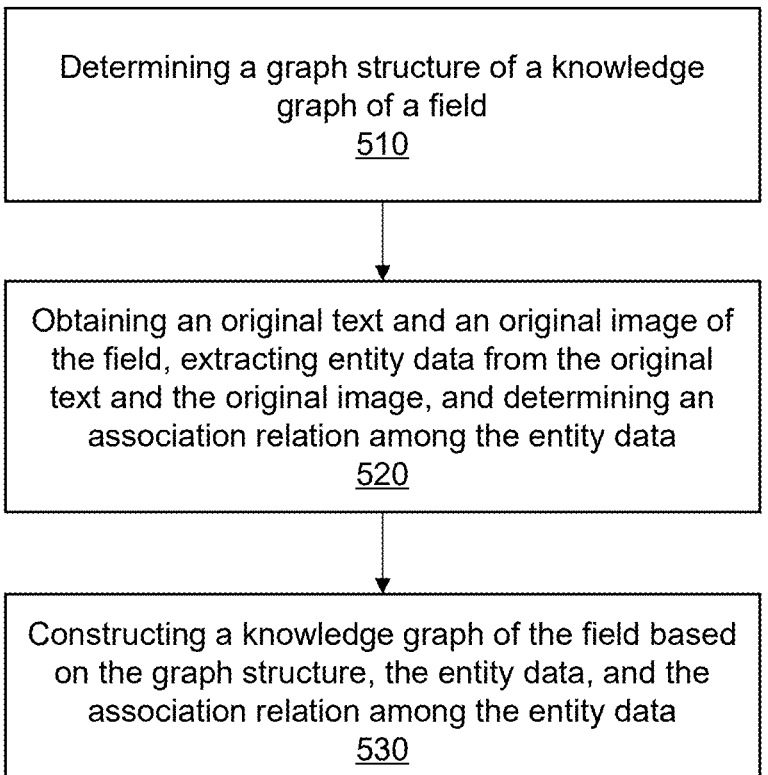

Determining a graph structure of a knowledge
graph of a field
510

Obtaining an original text and an original image of
the field, extracting entity data from the original
text and the original image, and determining an
association relation among the entity data
520

Constructing a knowledge graph of the field based
on the graph structure, the entity data, and the
association relation among the entity data
530

Figures 8, 9:
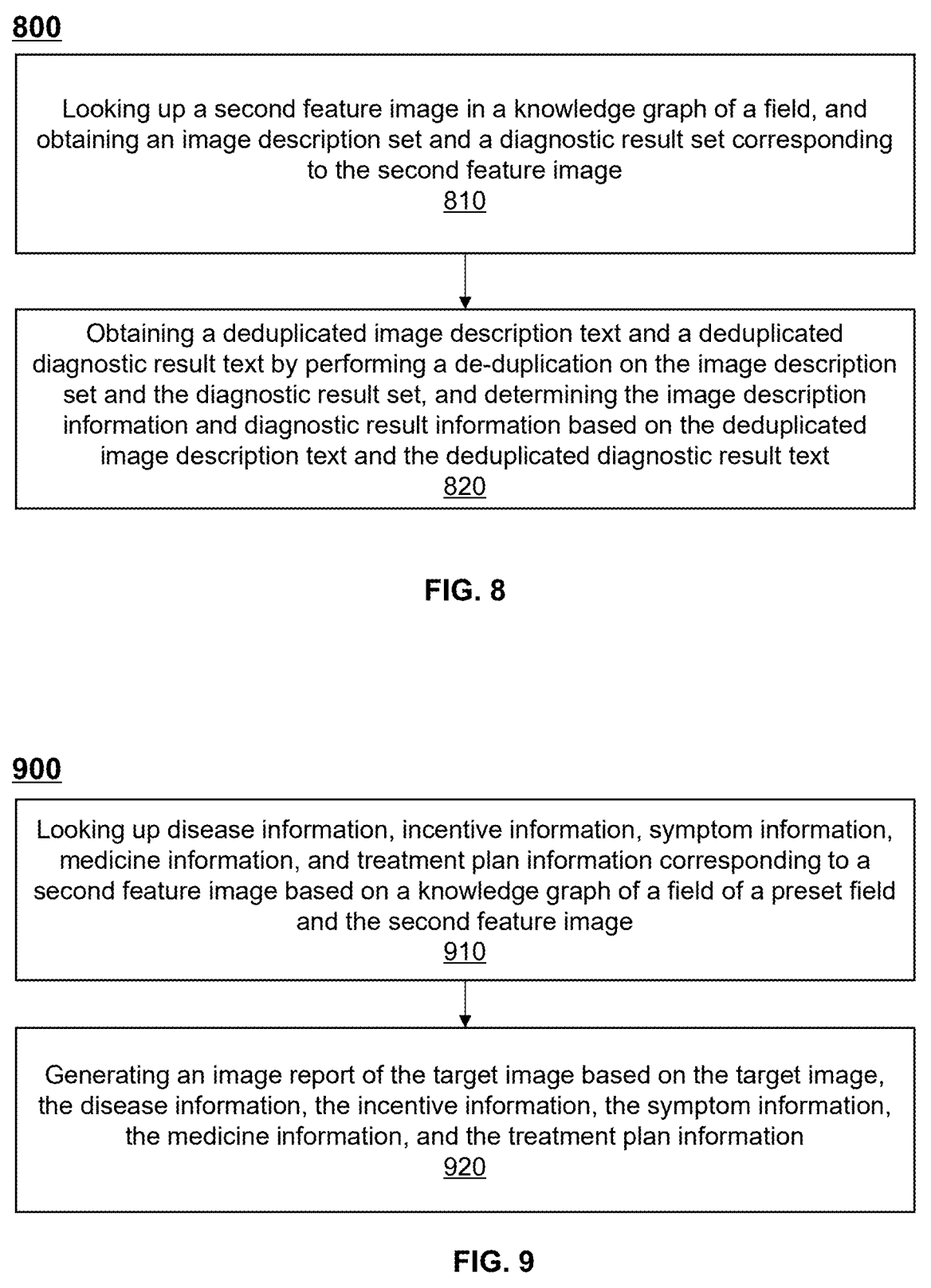

Looking up a second feature image in a knowledge graph of a field, and obtaining an image description set and a diagnostic result set corresponding to the second feature image
810

Obtaining a deduplicated image description text and a deduplicated diagnostic result text by performing a de-duplication on the image description set and the diagnostic result set, and determining the image description information and diagnostic result information based on the deduplicated image description text and the deduplicated diagnostic result text
820

Looking up disease information, incentive information, symptom information, medicine information, and treatment plan information corresponding to a second feature image based on a knowledge graph of a field of a preset field and the second feature image
910

Generating an image report of the target image based on the target image, the disease information, the incentive information, the symptom information, the medicine information, and the treatment plan information
920

Figure 10:
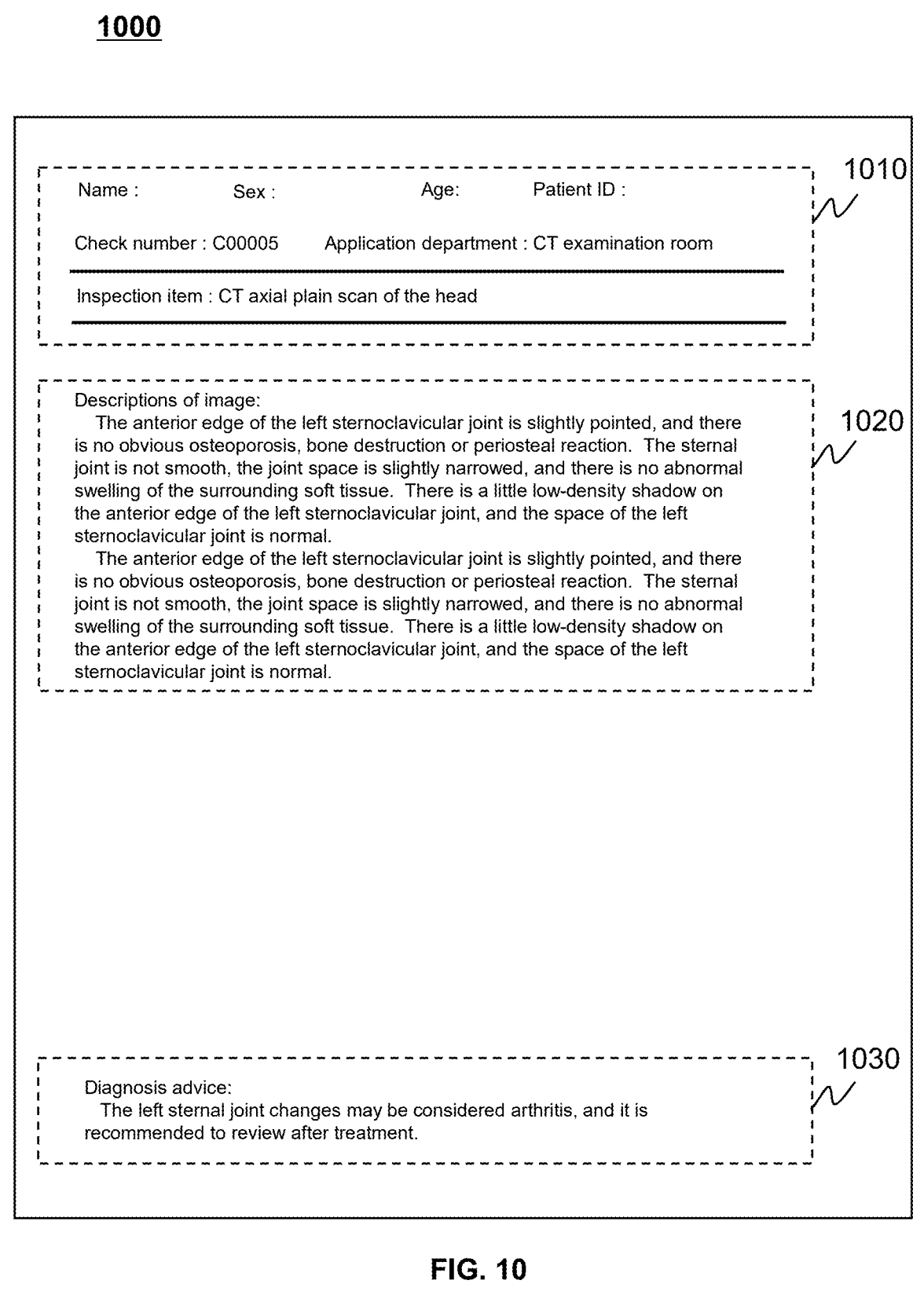

Name :          Sex :               Age:          Patient ID :

Check number : C00005          Application department : CT examination room

Inspection item : CT axial plain scan of the head

1010

Descriptions of image:
    The anterior edge of the left sternoclavicular joint is slightly pointed, and there is no obvious osteoporosis, bone destruction or periosteal reaction. The sternal joint is not smooth, the joint space is slightly narrowed, and there is no abnormal swelling of the surrounding soft tissue. There is a little low-density shadow on the anterior edge of the left sternoclavicular joint, and the space of the left sternoclavicular joint is normal.
    The anterior edge of the left sternoclavicular joint is slightly pointed, and there is no obvious osteoporosis, bone destruction or periosteal reaction. The sternal joint is not smooth, the joint space is slightly narrowed, and there is no abnormal swelling of the surrounding soft tissue. There is a little low-density shadow on the anterior edge of the left sternoclavicular joint, and the space of the left sternoclavicular joint is normal.

1020

Diagnosis advice:
    The left sternal joint changes may be considered arthritis, and it is recommended to review after treatment.

Figure 11:
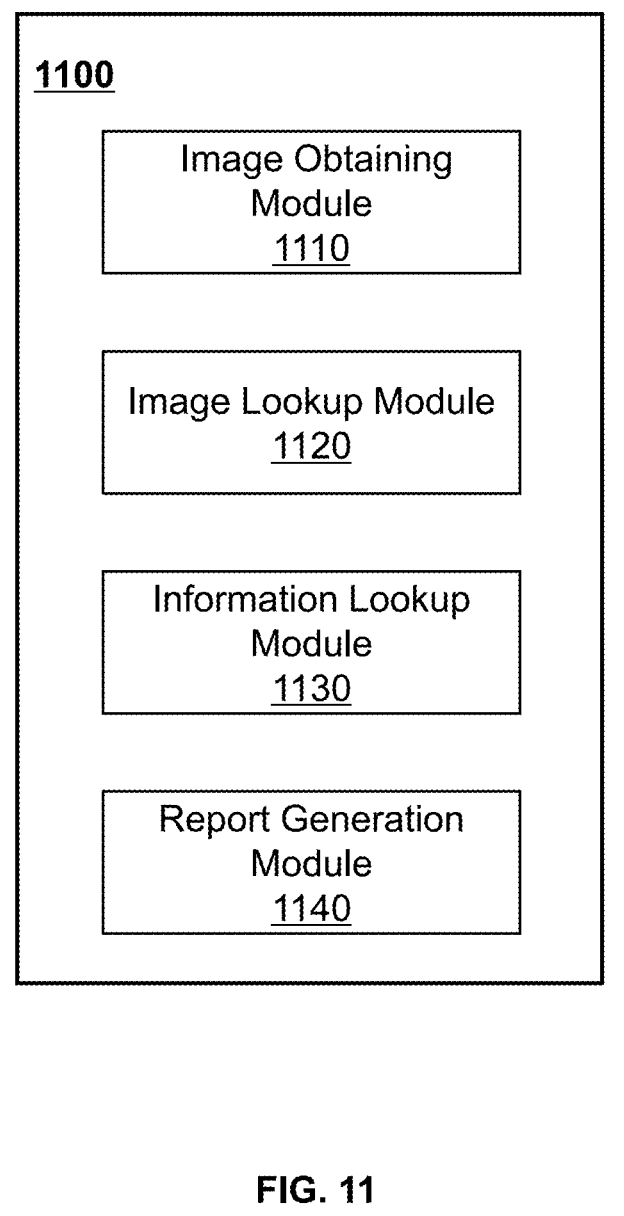

Image Obtaining
Module
1110

Image Lookup Module
1120

Information Lookup
Module
1130

Report Generation
Module
1140

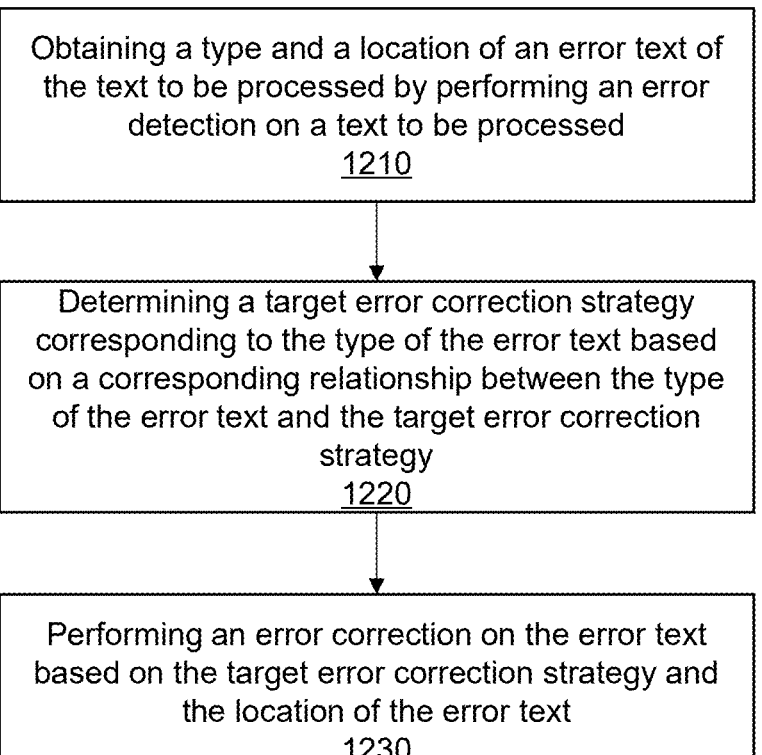

Obtaining a type and a location of an error text of the text to be processed by performing an error detection on a text to be processed
1210

Determining a target error correction strategy corresponding to the type of the error text based on a corresponding relationship between the type of the error text and the target error correction strategy
1220

Performing an error correction on the error text based on the target error correction strategy and the location of the error text
1230

FIG. 12A

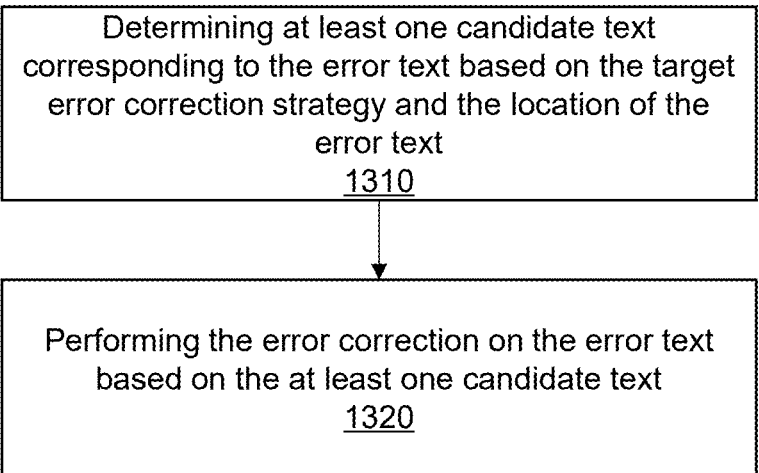

Determining at least one candidate text corresponding to the error text based on the target error correction strategy and the location of the error text
1310

Performing the error correction on the error text based on the at least one candidate text
1320

FIG. 13

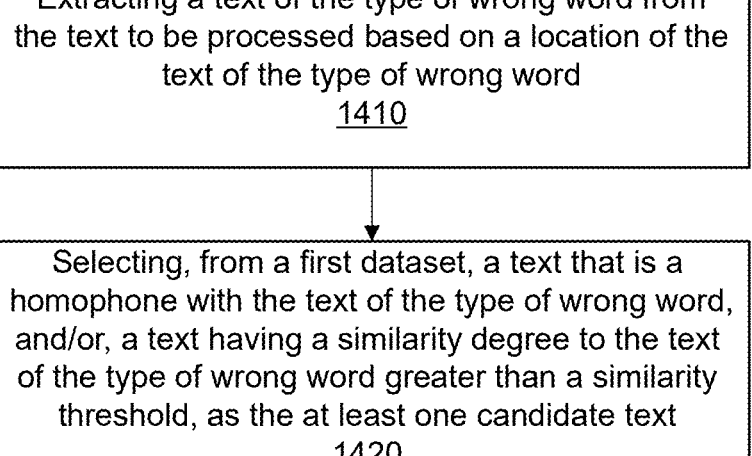

Extracting a text of the type of wrong word from the text to be processed based on a location of the text of the type of wrong word
1410

Selecting, from a first dataset, a text that is a homophone with the text of the type of wrong word, and/or, a text having a similarity degree to the text of the type of wrong word greater than a similarity threshold, as the at least one candidate text
1420

FIG. 14

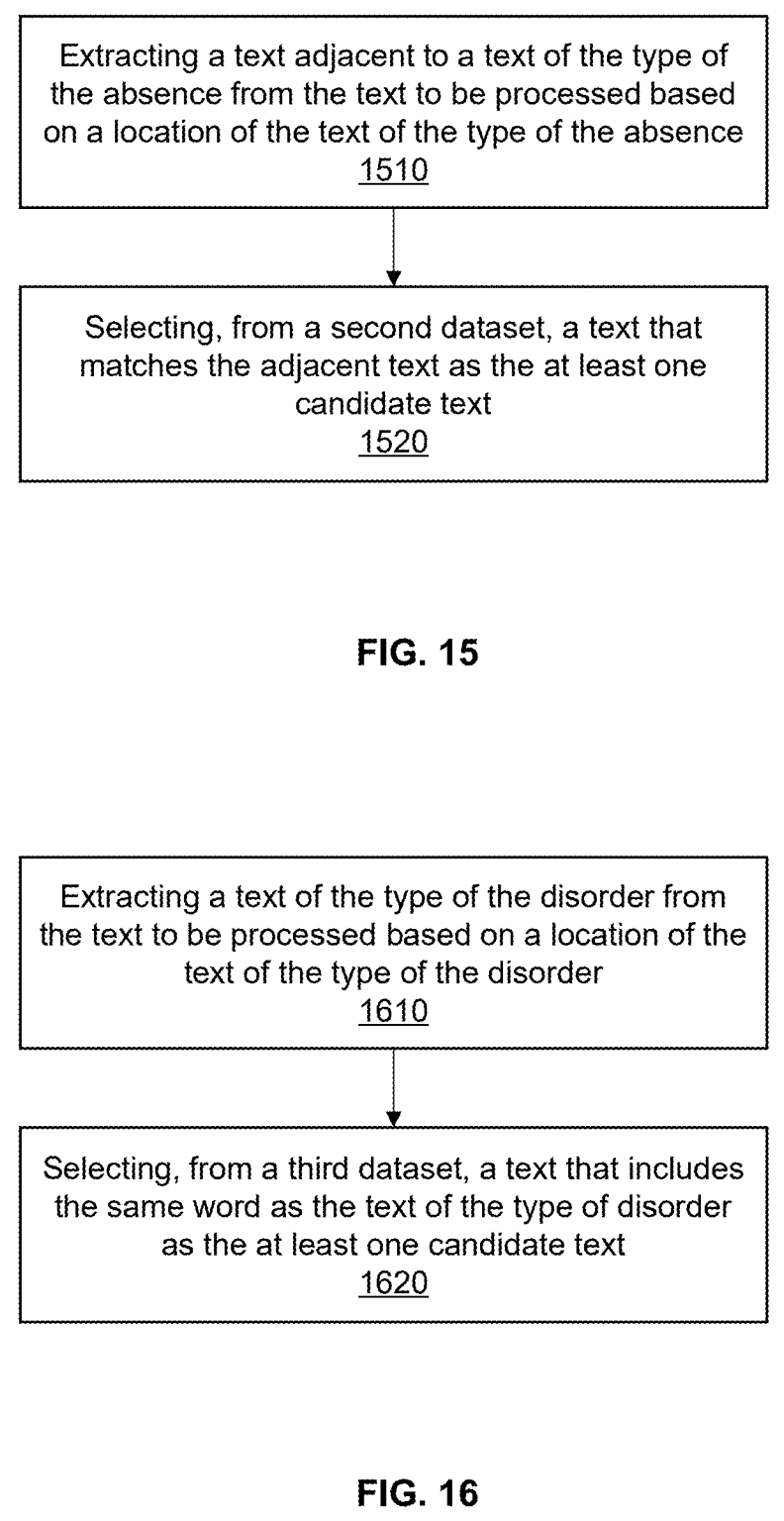

Extracting a text adjacent to a text of the type of
the absence from the text to be processed based
on a location of the text of the type of the absence
1510

Selecting, from a second dataset, a text that
matches the adjacent text as the at least one
candidate text
1520

FIG. 15

Extracting a text of the type of the disorder from
the text to be processed based on a location of the
text of the type of the disorder
1610

Selecting, from a third dataset, a text that includes
the same word as the text of the type of disorder
as the at least one candidate text
1620

FIG. 16

Adding the at least one candidate text to the corresponding location in the text to be processed, and determining a score of the at least one added text to be processed that indicates a fluency degree of the added text to be processed
1710

Ranking the at least one added text to be processed in a descending order based on the score of the at least one added text to be processed, and determining the added text to be processed that has a highest score as a corrected text
1720

FIG. 17

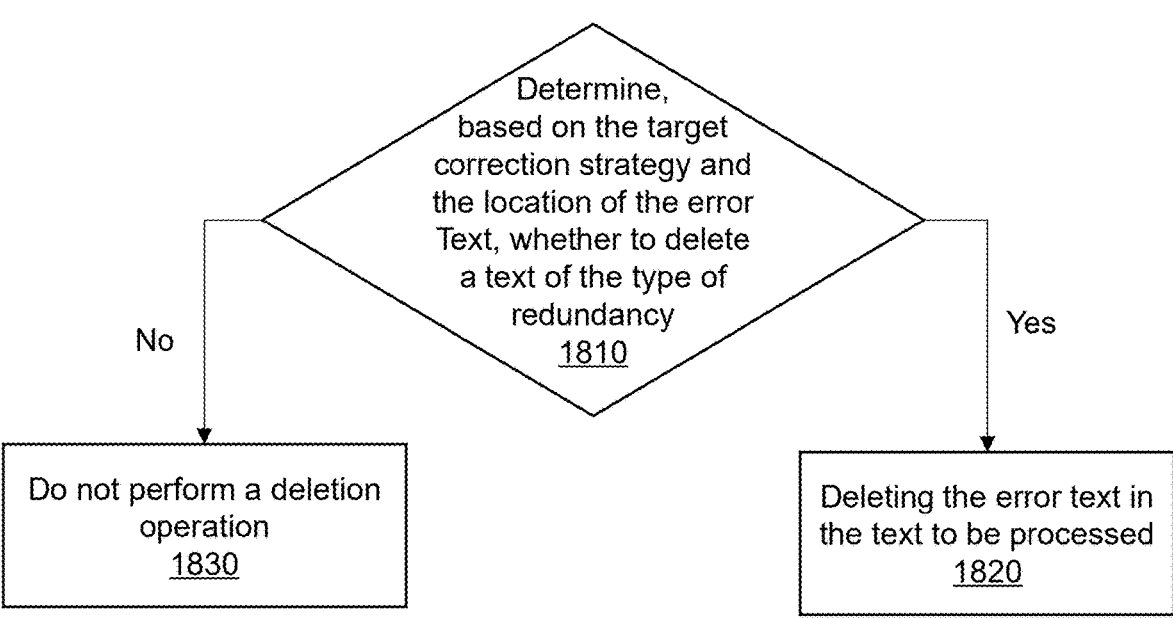

Determine, based on the target correction strategy and the location of the error Text, whether to delete a text of the type of redundancy
1810

No

Yes

Do not perform a deletion operation
1830

Deleting the error text in the text to be processed
1820

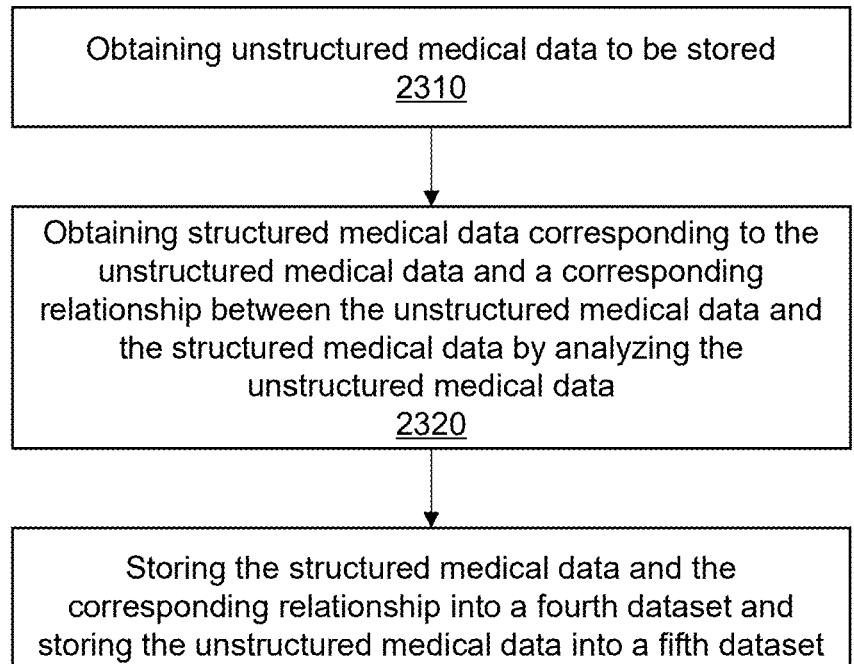

Obtaining unstructured medical data to be stored
2310

Obtaining structured medical data corresponding to the unstructured medical data and a corresponding relationship between the unstructured medical data and the structured medical data by analyzing the unstructured medical data
2320

Storing the structured medical data and the corresponding relationship into a fourth dataset and storing the unstructured medical data into a fifth dataset
2330

Obtaining the structured medical data corresponding to the unstructured medical data by analyzing the unstructured medical data using a preset analysis rule
2410

Constructing a corresponding relationship between the unstructured medical data and the structured medical data based on a data identifier of the unstructured medical data and a data identifier of the structured medical data
2420

Receiving a query request,  the query request including a data identifier
of data to be searched
<u>2510</u>

Obtaining the structured medical data and the unstructured medical data
corresponding to the data identifier, by looking in the fourth database
and the fifth database, respectively, according to the data identifier, the
corresponding relationship, and the query request
<u>2520</u>

FIG. 25

Obtaining Module
2710

Analysis Module
2720

Storage Module
2730

Unstructured Data Storage Device

SYSTEMS AND METHODS FOR MEDICAL DATA PROCESSING

CROSS-REFERENCE TO RELATED APPLICATIONS

This application a Continuation of International Application No. PCT/CN2021/106971 filed on Jul. 17, 2021, which claims priority to the following applications.

Chinese Patent Application No. 202010690317.8 filed on Jul. 17, 2020.

Chinese Patent Application No. 202011434314.4 filed on Dec. 10, 2020.

Chinese Patent Application No. 202011495360.5 filed on Dec. 17, 2020.

The entire contents of each of the above applications are hereby incorporated by reference.

TECHNICAL FIELD

This present disclosure generally relates to a medical field, and more particularly, relates to a medical data processing method and system.

BACKGROUND

With the development of the medical field, the processing of medical data becomes more and more important, for example, generation of a medical image report, correction of a medical text, and storage and lookup of medical data. Therefore, it is desirable to provide systems and methods for medical data processing, which may process the medical data efficiently and accurately.

SUMMARY

One aspect of the present disclosure provides a method implemented on a device including at least one storage device and at least one processing device. The method may comprise: obtaining a target image; obtaining a first feature image from the target image, the first feature image including a region of interest (ROI) in the target image; obtaining a second feature image that matches the first feature image; obtaining a knowledge graph, the knowledge graph including a relationship between the second feature image, and image description information and diagnostic result information corresponding to the second feature image; obtaining the image description information and the diagnostic result information corresponding to the second feature image based on the knowledge graph and the second feature image; and generating an image report of the target image based on the target image, the image description information, and the diagnostic result information.

In some embodiments, the knowledge graph may be provided by performing operations including: determining a graph structure of the knowledge graph; obtaining an original text and an original image of a preset field; extracting entity data from the original text and the original image; determining an association relation among the entity data; and determining the knowledge graph of the preset field based on the graph structure, the entity data, and the association relation.

In some embodiments, extracting the entity data from the original text and the original image may comprise: obtaining a plurality of word segmentation results outputted by a trained word segmentation model by inputting the original text into the trained word segmentation model; obtaining a plurality of feature texts outputted by a trained entity identification model by inputting the plurality of word segmentation results into the trained entity identification model; and determining the plurality of feature texts as the entity data.

In some embodiments, determining the association relation among the entity data may comprise: obtaining the association relation among the plurality of feature texts by inputting the original text and the plurality of feature texts into a trained relation extraction model.

In some embodiments, extracting the entity data from the original text and the original image may comprise: obtaining an identification result outputted by an identification model by inputting the original image into a trained identification model, the identification result being configured to indicate a region of interest in the original image; obtaining a feature image of the region of interest (ROI) in the original image; and determining the feature image of the original image as the entity data.

In some embodiments, extracting the entity data from the original text and the original image, and determining the association relation among the entity data may comprise: extracting, from the original text, an image description text and a diagnostic result text corresponding to the original image from the original text; extracting a feature image from the original image; determining the image description text, the diagnostic result text, and the feature image of the original image as the entity data; and determining the association relation among the feature image of the original image, the image description text, and the diagnostic result text.

In some embodiments, determining the knowledge graph of the preset field based on the graph structure, the entity data, and the association relation among the entity data may comprise: dividing the entity data into a plurality of triads based on the association relation among the entity data; and generating the knowledge graph by filling the plurality of triads into the graph structure.

In some embodiments, the method may further comprise: obtaining, based on the knowledge graph and the second feature image, at least one of disease information, incentive information, symptom information, medicine information, or treatment plan information corresponding to the second feature image; and generating the image report of the target image based on the at least one of the target image, the disease information, the incentive information, the symptom information, the medicine information, or the treatment plan information.

In some embodiments, the method may further comprise: obtaining a type and a location of an error text of the image report by performing an error detection on the image report of the target image; determining a target error correction strategy corresponding to the type of the error text based on a corresponding relationship between the type of the error text and the target error correction strategy; and performing an error correction on the error text based on the target error correction strategy and the location of the error text.

In some embodiments, the type of the error text may include at least one of a type of wrong word, a type of absence, or a type of disorder. Performing the error correction on the error text based on the target error correction strategy and the location of the error text may comprise: determining at least one candidate text corresponding to the error text based on the target error correction strategy and the location of the error text; and performing the error correction on the error text based on the at least one candidate text.

In some embodiments, the type of the error text includes the type of wrong word. Determining the at least one candidate text corresponding to the error text based on the target error correction strategy and the location of the error text may comprise: extracting a text of the type of wrong word from the image report based on a location of the text of the type of wrong word; and selecting, from a first database, a text that is a homophone with the type of wrong word, and/or, a text having a similarity degree to the text of the type of wrong word greater than a similarity threshold, as the at least one candidate text.

In some embodiments, the type of the error text includes the type of absence. Determining the at least one candidate text corresponding to the error text based on the target error correction strategy and the location of the error text comprises: extracting, from the image report based on a location of the text of the type of the absence, a text adjacent to a text of the type of the absence; and selecting, from a second database, a text that matches the adjacent text as the at least one candidate text.

In some embodiments, the type of the error text includes the type of disorder. Determining the at least one candidate text corresponding to the error text based on the target error correction strategy and the location of the error text may comprise: extracting a text of the type of disorder from the image report based on a location of the text of the type of disorder; and selecting, from a third database, a text that includes one or more same words as the text of the type of disorder as the at least one candidate text.

In some embodiments, performing the error correction on the error text based on the at least one candidate text may comprise: obtaining at least one added text to be processed by adding the at least one candidate text to the corresponding location of the error text; determining a score of each of the at least one added text to be processed that indicates a fluency degree of the added text to be processed; and ranking the at least one added text to be processed in a descending order based on the score of the at least one added text to be processed.

In some embodiments, the type of the error text includes a type of redundancy. Determining the at least one candidate text corresponding to the error text based on the target error correction strategy and the location of the error text comprises: determining whether to delete a text of the type of redundancy based on the target correction strategy and the location of the error text; in response to a determination of deleting the text of the type of redundancy, deleting the error text; or in response to a determination of not deleting the text of the type of redundancy, retaining the error text.

In some embodiments, determining whether to delete the text of the type of redundancy based on the target correction strategy and the location of the error text may comprise: extracting the text of the type of redundancy from the image report based on a location of the text of the type of redundancy; detecting whether the text of the type of redundancy is smooth; in response to determining that the text of the type of redundancy is not smooth, deleting the text of type redundancy; or in response to determining that the text of the type of redundancy is smooth, retaining the text of type redundancy.

In some embodiments, the image report may be unstructured medical data, the method further may comprise: obtaining structured medical data corresponding to the image report and a corresponding relationship between the image report and the structured medical data by analyzing the image report; storing the structured medical data and the corresponding relationship into a fourth database; and storing the image report into a fifth database.

In some embodiments, obtaining the structured medical data corresponding to the image report and the corresponding relationship between the image report and the structured medical data by analyzing the image report may comprise: obtaining a corresponding analysis rule from a plurality of preset analysis rules based on an unstructured medical data type of the image report; obtaining the structured medical data corresponding to the image report by analyzing the image report based on the corresponding analysis rule; and determining the corresponding relationship between the image report and the structured medical data based on a data identifier of the unstructured medical data of the image report and a data identifier of the structured medical data.

In some embodiments, the plurality of preset analysis rules may include at least one of a medical image text identification rule, a Digital Imaging and Communications in Medicine (DICOM) file analysis rule, or an Extensive Markup Language (XML) report analysis rule.

In some embodiments, the method further may comprise: obtaining the image report sent by a corresponding medical device through a preset application interface; or, obtaining the image report by accessing, based on a target address identifier, a medical device corresponding to the target address identifier.

In some embodiments, the method further may comprise: receiving a query request, the query request including a data identifier of the image report; and obtaining, based on the data identifier, the corresponding relationship, and the query request, the structured medical data and the image report corresponding to the data identifier by accessing the fourth database and the fifth database.

In some embodiments, obtaining, based on the data identifier, the corresponding relationship, and the query request, the structured medical data corresponding to the data identifier and the image report by accessing the fourth database and the fifth database may comprise: obtaining, based on the data identifier and the query request, the structured medical data corresponding to the data identifier by accessing the fourth database; and obtaining the image report from the fifth database based on the structured medical data corresponding to the data identifier and the corresponding relationship.

Another aspect of the present disclosure provides a system. The system may include at least one storage device includes a set of instructions, and at least one processor configured to communicate with the at least one storage device. When executing the set of instructions, the at least one processor is configured to direct the system to perform at least one operation including: obtaining a target image; obtaining a first feature image from the target image, the first feature image including a region of interest (ROI) in the target image; obtaining a second feature image that matches the first feature image; obtaining a knowledge graph, the knowledge graph including a relationship between the second feature image, and image description information and diagnostic result information corresponding to the second feature image; obtaining the image description information and the diagnostic result information corresponding to the second feature image based on the knowledge graph and the second feature image; and generating an image report of the target image based on the target image, the image description information, and the diagnostic result information.

Another aspect of the present disclosure provides a system. The system may include an image obtaining module configured to obtain a target image, and obtain a first feature image from the target image, wherein the first feature image includes a region of interest (ROI) in the target image. The system may include an image lookup module configured to obtain a second feature image that matches the first feature image. The system may include an information lookup module configured to obtain a knowledge graph, the knowledge graph including a relationship between the second feature image, and image description information and diagnostic result information corresponding to the second feature image; and obtain the image description information and the diagnostic result information corresponding to the second feature image based on the knowledge graph and the second feature image. The system may further include a report generation module configured to generate an image report of the target image based on the target image, the image description information, and the diagnostic result information.

Another aspect of the present disclosure provides a non-transitory computer readable medium comprising at least one set of instructions. when executed by one or more processors of a computing device, the at least one set of instruction sets may direct the computing device to perform a method. The method may comprise: obtaining a target image; obtaining a first feature image from the target image, the first feature image including a region of interest (ROI) in the target image; obtaining a second feature image that matches the first feature image; obtaining a knowledge graph, the knowledge graph including a relationship between the second feature image, and image description information and diagnostic result information corresponding to the second feature image; obtaining the image description information and the diagnostic result information corresponding to the second feature image based on the knowledge graph and the second feature image; and generating an image report of the target image based on the target image, the image description information, and the diagnostic result information.

Another aspect of the present disclosure provides a data processing method implemented on a device including at least one storage device and at least one processing device, wherein the method comprises: obtaining a type and a location of an error text by performing an error detection on a text to be processed; determining a target error correction strategy corresponding to the type of the error text based on a corresponding relationship between the type of the error text and the target error correction strategy; and performing an error correction on the error text based on the target error correction strategy and the location of the error text.

Another aspect of the present disclosure provides a data processing system, including: at least one storage device including a set of instructions; at least one processor configured to communicate with the at least one storage device, wherein when executing the set of instructions, the at least one processor is configured to direct the system to perform operations including: obtaining a type and a location of an error text by performing an error detection on a text to be processed; determining a target error correction strategy corresponding to the type of the error text based on a corresponding relationship between the type of the error text and the target error correction strategy; and performing an error correction on the error text based on the target error correction strategy and the location of the error text.

Another aspect of the present disclosure provides a data processing system, comprising: a detection module configured to obtain a type and a location of an error text of the image report by performing an error detection on a text to be processed; a determination module configured to determine a target error correction strategy corresponding to the type of the error text based on a corresponding relationship between the type of the error text and the target error correction strategy; and an error correction module configured to perform an error correction on the error text based on the target error correction strategy and the location of the error text.

Another aspect of the present disclosure provides a non-transitory computer readable medium comprising at least one set of instructions, wherein when executed by one or more processors of a computing device, the at least one set of instruction sets direct the computing device to perform a method, the method comprises: obtaining a type and a location of an error text of the image report by performing an error detection on a text to be processed; determining a target error correction strategy corresponding to the type of the error text based on a corresponding relationship between the type of the error text and the target error correction strategy; and performing an error correction on the error text based on the target error correction strategy and the location of the error text.

Another aspect of the present disclosure provides a method for storing unstructured data implemented on a device including at least one storage device and at least one processing device, wherein the method may comprise: obtaining unstructured medical data to be stored; obtaining structured medical data corresponding to the unstructured medical data and a corresponding relationship between the unstructured medical data and the structured medical data by analyzing the unstructured medical data; storing the structured medical data and the corresponding relationship into a fourth database; and storing the unstructured medical data into a fifth database.

Another aspect of the present disclosure provides a system for storing unstructured data. The system may include at least one storage device includes a set of instructions; at least one processor configured to communicate with the at least one storage device. When executing the set of instructions, the at least one processor may be configured to direct the system to perform operations including: obtaining unstructured medical data to be stored; obtaining structured medical data corresponding to the unstructured medical data and a corresponding relationship between the unstructured medical data and the structured medical data by analyzing the unstructured medical data; storing the structured medical data and the corresponding relationship into a fourth database; and storing the unstructured medical data into a fifth database.

Another aspect of the present disclosure provides a system for storing unstructured data may include: an obtaining module configured to obtain unstructured medical data to be stored; a analysis module configured to obtain structured medical data corresponding to the unstructured medical data and a corresponding relationship between the unstructured medical data and the structured medical data by analyzing the unstructured medical data; and a storage module configured to store the structured medical data and the corresponding relationship into a fourth database, and storing the unstructured medical data into a fifth database.

Another aspect of the present disclosure provides a non-transitory computer readable medium comprising at least one set of instructions. When executed by one or more processors of a computing device, the at least one set of instruction sets may direct the computing device to perform a method. The method may comprise: obtaining unstructured medical data to be stored; obtaining structured medical data corresponding to the unstructured medical data and a corresponding relationship between the unstructured medical data and the structured medical data by analyzing the unstructured medical data; storing the structured medical data and the corresponding relationship into a fourth database; and storing the unstructured medical data into the fifth database.

BRIEF DESCRIPTION OF THE DRAWINGS

The drawings described herein are used to provide a further understanding of the present disclosure. The schematic embodiments of the present disclosure and the description thereof will be described herein to explain the present disclosure, but not limited to the present disclosure. In the drawings, the same reference numerals represent the same structures.

FIG. 4 is a flowchart illustrating an exemplary imaging report generation process according to some embodiments of the present disclosure;

FIG. 5 is a flowchart illustrating an exemplary process for constructing a knowledge graph of a field according to some embodiments of the present disclosure;

FIG. 8 is a flowchart illustrating an exemplary process for obtaining image description information and diagnostic result information corresponding to a target image according to some embodiments of the present disclosure;

FIG. 9 is a flowchart illustrating an exemplary process for generating an image report according to some embodiments of the present disclosure;

FIG. 10 is a schematic diagram illustrating an exemplary image report according to some embodiments of the present disclosure;

FIG. 11 is a block diagram illustrating an exemplary image report generation device according to some embodiments of the present disclosure;

FIG. 12A is a flowchart illustrating an exemplary text correction process according to some embodiments of the present disclosure;

FIG. 13 is a flowchart illustrating an exemplary process for performing an error correction on an error text based on a target error correction strategy and a location of an error text according to some embodiments of the present disclosure;

FIG. 14 is a flowchart illustrating an exemplary process for determining at least one candidate text corresponding to an error text based on a target error correction strategy and a location of the error text according to some embodiments of the present disclosure;

FIG. 15 is a flowchart illustrating an exemplary process for determining at least one candidate text corresponding to an error text based on a target error correction strategy and a location of the error text according to some embodiments of the present disclosure;

FIG. 16 is a flowchart illustrating an exemplary process for determining at least one candidate text corresponding to an error text based on a target error correction strategy and a location of the error text according to some embodiments of the present disclosure;

FIG. 17 is a flowchart illustrating an exemplary process for performing an error correction on an error text based on a target error correction strategy and a location of the error text according to some embodiments of the present disclosure;

FIG. 18 is a flowchart illustrating an exemplary process for performing an error correction on an error text based on a target error correction strategy and a location of the error text according to some embodiments of the present disclosure;

FIG. 23 is a flowchart illustrating an exemplary unstructured data storage process according to some embodiments of the present disclosure;

FIG. 24 is a flowchart illustrating an exemplary unstructured data storage process according to some embodiments of the present disclosure;

FIG. 25 is a flowchart illustrating an exemplary unstructured data storage process according to some embodiments of the present disclosure;

FIG. 27 is a schematic diagram illustrating an exemplary unstructured data storage device according to some embodiments of the present disclosure.

DETAILED DESCRIPTION

Figure 1:
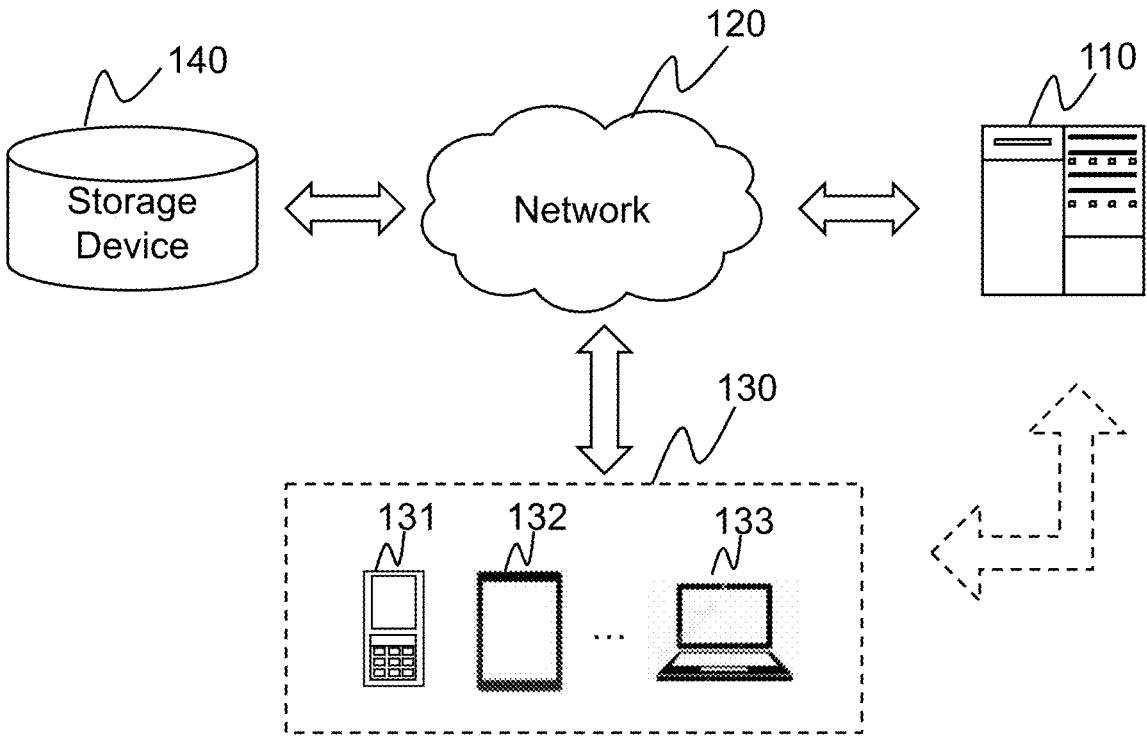
FIG. 1 is a schematic diagram illustrating an application scenario of a medical system according to some embodiments of the present disclosure.

In order to illustrate technical solutions of the embodiments of the present disclosure, a brief introduction regarding the drawings used to describe the embodiments is provided below. Obviously, the drawings described below are merely some examples or embodiments of the present disclosure. Those having ordinary skills in the art, without further creative efforts, may apply the present disclosure to other similar scenarios according to these drawings. It should be understood that the exemplary embodiments are provided merely for better comprehension and application of the present disclosure by those skilled in the art, and not intended to limit the scope of the present disclosure. Unless obvious according to the context or illustrated specifically, the same numeral in the drawings refers to the same structure or operation.

As used in the disclosure and the claims, the singular forms "a," "an," and "the" may be intended to include the plural forms as well, unless the context clearly indicates otherwise. In general, it will be further understood that the terms "comprise" and/or "include" specify the presence of stated operations and elements, but do not preclude the presence or addition of other operations or elements.

Through the present disclosure makes various references to some modules of a system according to embodiments of the present disclosure, any number of different modules may be used and applied to a client and/or a server. The module (s) is merely for illustration, and different aspects of the system and method may use different modules.

A flowchart is used in the present disclosure to illustrate the operations performed by the system according to the embodiment of the present disclosure. It should be understood that previous or following operations are not necessarily performed in order. Instead, various operations may be processed in reverse or simultaneously. At the same time, other operations may also be added to these processes, or one or more operations may be removed from these processes.

One aspect of the present disclosure provides an image report generation method, system, processing device, and storage medium for: obtaining a target image; obtaining a first feature image from the target image; obtaining a second feature image that matches the first feature image by accessing a preset feature image database based on the first feature image; obtaining image description information and diagnostic result information corresponding to the target image based on a preset knowledge graph of a field and the second feature image; and generating an image report based on the target image, the image description information, and the diagnostic result information. In the present disclosure, an image report may be automatically generated using a pre-constructed knowledge graph of a field. Compared with the prior art, a doctor may not need to write the image report manually, thereby improving the efficiency for generating the image report.

Another aspect of the present disclosure provides a data processing method, system, processing device, and storage medium for: obtaining a type and a location of an error text by performing an error detection on a text to be processed; determining a target error correction strategy corresponding to the type of the error text based on a corresponding relationship between the type of the error text and the target error correction strategy; and performing an error correction on the error text based on the target error correction strategy and the location of the error text. In the above data processing method regarding error correction, since each type of error text corresponds to its respective target error correction strategy, each type of error text may be corrected through the corresponding error correction. In the prior art, any types of error text may utilize a correction text through big data, which may result in a large amount of data for processing and a poor error correction accuracy. Compared to the prior art, the present disclosure may improve the accuracy of the error correction and a speed of data processing.

Yet another aspect of the present disclosure provides an unstructured data storage method, system, processing device, and storage medium for: obtaining structured medical data corresponding to unstructured medical data to be stored and a corresponding relationship between the unstructured medical data and the structured medical data by analyzing the unstructured medical data; and storing the structured medical data and the corresponding relationship into a preset database (e.g., a fourth database illustrated in FIG. 23), and storing the unstructured medical data to be stored into another preset database (e.g., a fifth database illustrated in FIG. 23). Since a process for analyzing the unstructured medical data is simple, the structured medical data corresponding to the unstructured medical data to be stored and the corresponding relationship between the unstructured medical data and the structured medical data may be obtained quickly and accurately. In this way, the structured medical data and the corresponding relationship may be stored into the preset database quickly, and the unstructured medical data to be stored may be stored into another preset database quickly, thereby improving the efficiency of storing the unstructured medical data.

FIG. 1 is a schematic diagram illustrating an application scenario of a medical system 100 according to some embodiments of the present disclosure. In some embodiments, the medical system 100 may include a data processing system 110, a network 120, a user terminal 130, and a storage device 140.

The data processing system 110 may be used to process medical data of the medical system 100. The data processing system 110 may include at least one of a picture archiving and communication system (PACS), a post-processing workstation, a surgical system, a hospital information system (HIS), a laboratory information system (LIS), a radiological information system (RIS), a doctor workstation, a nurse workstation, an imaging system, a hospitalization management systems, an outpatient and emergency management systems, a toll collection systems, or the like, or any combination thereof.

In some embodiments, the data processing system 110 may include one or more servers. The server may be used to manage resources and process data and/or information from at least one component or an external system of the system. In some embodiments, the server may be a single server or a server group. The server group may be a centralized or distributed (e.g., the server may be a distributed system). In some embodiments, the server may be local or remote. For example, the server may access information and/or information stored in storage device 140 through the network 120. In some embodiments, the server may be executed on a cloud platform. For example, the cloud platform may include a private cloud, a public cloud, a hybrid cloud, a community cloud, a distributed cloud, an inter-cloud, or the like, or a combination thereof.

In some embodiments, the server may include a processing device. In some embodiments, the processing device may include one or more sub-processing devices (e.g., a single core processing device or a multi-core processing device). For example, the processing device may include a central processor (CPU), an application specific integrated circuits (ASICs), an application-specific instruction-set processor (ASIP), a graphics processing unit (GPU), a physics processing unit (PPU), a digital signal processor (DSP), a field programmable gate array (FPGA), a programmable logic device (PLD), controller, a microcontroller unit, a reduced instruction set computer (RISC), a microprocessor, or the like, or any combination thereof.

The various components of the medical system 100 may be exchange data and/or information through the network 120. In some embodiments, one or more components (e.g., the data processing system 110, the user terminal 130, the storage device 140) of the medical system 100 may transmit data and/or information to other components of the medical system 100 via the network 120. In some embodiments, the network 120 may be any type of wired or wireless network. For example, network 120 may include a cable network, a wireline network, a fiber-optic network, a telecommunications network, an intranet, an internet, a local area network (LAN), a wide area network (WAN), a wireless local area network (WLAN), a metropolitan area network (MAN), a public telephone switched network (PSTN), a Bluetooth network, a ZigBee network, a near field communication (NFC) network, or the like, or a combination thereof. In some embodiments, the network 120 may include one or more network access points. For example, the network 120 may include wired and/or wireless network access points such as base stations and/or internet exchange points through which one or more components of the medical system 100 may be connected to the network 150 to exchange data and/or information.

The user terminal 130 may interact with the data processing system 110. In some embodiments, the user terminal 130 may receive data and/or information from the storage device 140 and/or the data processing system 110. In some embodiments, the user terminal 130 may include a mobile phone 131, a tablet 132, a laptop 133, or the like, or any combination thereof. In some embodiments, the user terminal 130 may establish communication with the data processing system 110 through an application software in the user terminal 130. For example, the user terminal 130 may receive data and/or information from the storage device 140 and/or data processing system 110 through the application software. For example, the user terminal 130 may send instructions and/or requests to the storage device 140 and/or the data processing system 110 through the application software.

One or more components of the medical system 100 may access the data or instructions stored in the storage device 140 via the network 120. The data refers to a digital representation of information, which may include various types, such as binary data, text data, image data, video data, or the like. The instruction refers to a program that controls a control device or a component to perform a specific function. The storage device 140 may be connected to the network 120 to communicate with one or more components of the medical system 100 (e.g., the data processing system 110, the user terminal 130). In some embodiments, the storage device 140 may be part of a server. The storage device 140 may be implemented in a single central server, a plurality of servers or individual devices connected through a communication link. The storage device 140 may be generated by a plurality of personal devices and cloud servers. In some embodiments, the storage device 140 may include a mass storage device, a removable storage device, a volatile read-and-write memory (e.g., a random access memory (RAM), a read-only memory (ROM)), or the like, or any combination thereof. In some embodiments, a database may be implemented on a cloud platform. For example, the cloud platform may include a private cloud, a public cloud, a hybrid cloud, a community cloud, a distributed cloud, an inter-cloud, or the like, or a combination thereof.

Figure 2:
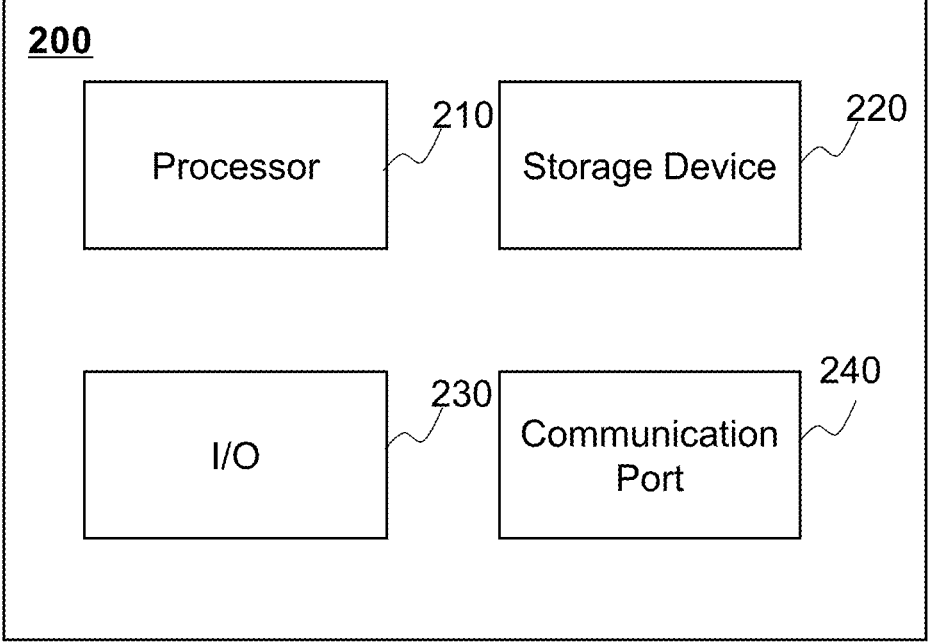
FIG. 2 is a schematic diagram illustrating exemplary hardware and/or software of a computing device according to some embodiments of the present disclosure.

FIG. 2 is a schematic diagram illustrating exemplary hardware and/or software of a computing device 200 according to some embodiments of the present disclosure. As shown in FIG. 2, the computing device 200 may include a processor 210, a storage device 220, an input/output (I/O) interface 230, and a communication port 240. In some embodiments, a server of the data processing system 110 may be implemented in accordance with the computing device 200.

The processor 210 may execute computer instructions (e.g., program code) and perform functions of the medical system 100 in accordance with techniques described herein. The computer instructions may include, for example, routines, programs, objects, components, data structures, procedures, modules, and functions (the functions refer to particular functions described herein). For example, the processor 210 may process a target image obtained from any component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof. Merely for illustration, only one processor is described in the computing device 200. However, it should be noted that the computing device 200 in the present disclosure may also include multiple processors.

The storage device 220 may store data/information obtained from any other component of the medical system 100. In some embodiments, storage device 220 may include a mass storage device, a removable storage device, a volatile read-and-write memory, a read-only memory (ROM), or the like, or a combination thereof. Exemplary mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc.

The input/output interface (I/O) 230 may be used to input or output signals, data, or information. In some embodiments, the I/O interface 230 may enable the user to contact the medical system 100. In some embodiments, the input/output interface (I/O) 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), or the like, or a combination thereof. The communication port 240 may be connected to a network to facilitate data communications. The connection may be a wired connection, a wireless connection, or a combination of both. The wired connection may include, for example, an electrical cable, an optical cable, a telephone wire, or the like, or a combination thereof. The wireless connection may include, for example, a Bluetooth link, a Wi-Fi link, a WiMax link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
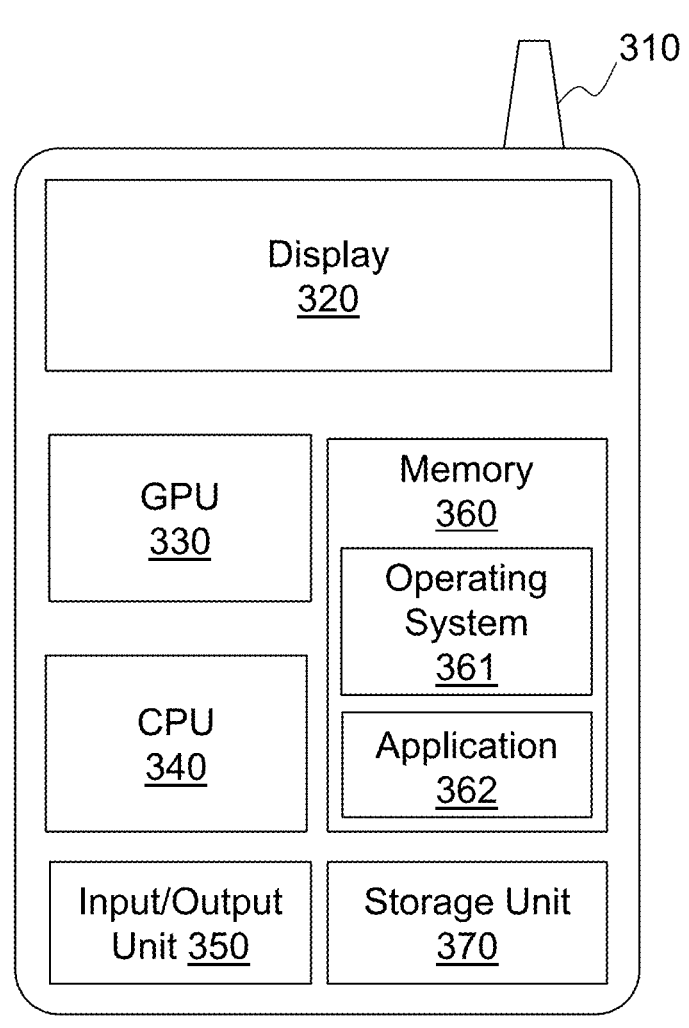
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. The mobile device 300 may be configured to implement a specific system disclosed in the present disclosure, for example, the user terminal 130. In this embodiment, the user device that is used to display and interact with location-related information may be a mobile device 300, including but not limited to, a smart phone, a tablet computer, a music player, a portable game console, and a global positioning system (GPS) receiver, a wearable computing device (such as glasses, a watch, etc.), or the like. The mobile device 300 in this embodiment may include one or more central processing units (CPUs) 340, graphic processing units (GPUs) 330, a display unit 320, a memory 360, an antenna 310 (for example, a wireless communication unit), a storage unit 370, and one or more input/output (I/O) units 350. Any other suitable components may include but not limited to a system bus or a controller (not shown in the figure), and may also be included in the mobile device 300. As shown in FIG. 3, a mobile operating system 361, such as iOS, Android, Windows Phone, etc., and one or more applications 362 may be loaded from the storage unit 370 into the memory 360 and executed by the CPU 340. The application 362 may include a browser or other mobile applications suitable for receiving and processing image reports on the mobile device 300. An interaction of a user (for example, doctor) about the image report may be obtained through the input/output (I/O) unit 350 and provided to the server 120 and/or other components of the medical system 100, for example, through the network 120.

In order to implement different modules, the units and their functions described in the above descriptions, a computer hardware platform may be used as a hardware platform for one or more of the elements described above (for example, a server, and/or other components of the medical system 100). The hardware elements, operating systems, and programming languages of such computers may be common in nature. It can be assumed that those skilled in the art are sufficiently familiar with these technologies to be able to use the technologies described herein to provide information required for an on-demand service. A computer including a user interface element may be used as a personal computer (PC) or other types of workstations or terminal devices, and may also be used as a server after being properly programmed. It should be understood that those skilled in the art are familiar with such structures, programs, and general operations of such computer equipment, and all drawings do not require additional explanations.

With the development of medical imaging devices, the role of medical imaging in a clinical diagnosis is increasingly important. Typically, after a medical image is generated, an image report may be generated based on the medical image. The existing image report may be generated by filling an obtained medical image into a pre-supplied image report template, and a pending part to be filled of the template may be manually filled by a doctor who reads the medical image. However, the existing image report generation method may have low efficiency. The present disclosure provides methods and systems that automatically generates an image report.

FIG. 4 is a flowchart illustrating an exemplary imaging report generation process according to some embodiments of the present disclosure. In some embodiments, the process 400 may be performed by the medical system 100 (e.g., the data processing system 110). For example, the process 400 may be performed by a server of a PACS, an imaging system, or a post-processing workstation. For example, the process 400 may be executed by the processor 210. As another example, the process 400 may be executed by one or more modules shown in FIG. 11. In some embodiments, the process 400 may be stored in the storage device (e.g., the storage device 140) in the form of a program or instruction, and the process 400 may be implemented when the medical system 100 executes the program or instruction. The operational schematic of the process 400 presented below is illustrative. In some embodiments, the process may be accomplished with one or more additional operations not described, and/or without one or more of the operations discussed. In addition, an order of operation of the process 400 as below and the following description is not intended to be limiting.

In 410, the data processing system 110 (e.g., an image obtaining module 1110) may obtain a target image and obtain a first feature image from the target image.

In some embodiments, the target image may include a medical image generated by an imaging system, such as at least one of a computed tomography (CT) image, a magnetic resonance (MR) image, a positron emission computed tomography (PET) image, an X-ray image, an ultrasonic image, or the like. In the present disclosure, the feature image may refer to an image of a region of interest. The region of interest may be a whole or a portion of an object (e.g., a human body, an animal, a physical object, etc.), such as a head, a chest, an abdomen, a heart, a liver, an upper limb, a lower limb, a spine, a bone, a blood vessel, a lesion, tumor parts, or the like, or any combination thereof. The first feature image may be part of the target image. For example, the target image may be a CT image of a certain cross section of an abdomen of the object, and the first feature image may be an image of a liver in the CT image of the abdomen.

In some embodiments, there are a variety of ways to acquire the target image, for example, obtaining the target image from an imaging device through the network 120, or obtaining the target image from an image database (e.g., the storage device 140, the storage device 220, the PACS, etc.) through the network 120. The embodiments in the present disclosure does not limit the acquisition ways of the target image.

In some embodiments, after obtaining the target image, the region of interest in the target image may be identified, and an image of the region of interest may be segmented from the target image and determined as the first feature image.

In some embodiments, a method for determining the region of interest may include: inputting the target image into a trained identification model and obtain the region of interest of the target image outputted by the identification model. Another method for determining the region of interest may include that: the user manually selects the region of interest in the target image. The data processing system 110 receives the selection operation of the target image from the user terminal 130, and determine the region of interest in the target image according to the selection operation, thereby obtaining the first feature image. The embodiment of the present disclosure does not limit the method for determining the region of interest.

In 420, the data processing system 110 (e.g., an image lookup module 1120) may obtain a second feature image that matches the first feature image by looking, based on the first feature image, in a preset feature image database.

In some embodiments, the feature image database (for example, the PACS, the storage device 140, the storage device 220) may include a plurality of feature images, such as at least one of a CT image, an MR image, a PET image, an X-ray image, and an ultrasound image.

In some embodiments, the feature image database may be preset. After the first feature image is segmented from the target image, the data processing system 110 may determine a similarity degree between the first feature image and each feature image in the feature image database, thereby determining a plurality of similarity degrees. The data processing system 110 may determine a feature image in the feature image database that satisfies a preset condition as a second feature image. The preset condition may include a similarity degree greater than a preset threshold (e.g., 30%, 40%, 50%, 60%, 70%, 80%, 90%, 95%).

For example, a similarity degree 1 (e.g., 96%) between the first feature image A and a feature image 1 in the feature image database may be determined, a similarity degree 2 (e.g., 70%) between the first feature image A and a feature image 2 in the feature image database may be determined, and so on. If the preset threshold is set to 95%, the feature image in the feature image database having a similarity degree greater than 95% may be determined as the second feature image, for example, the feature image 1.

In some embodiments, the similarity degree between the feature image in the feature image database and the first feature image may be determined through at least one of an image type (for example, a CT image, an MR image, a PET image, an X-ray image, an ultrasound image), a type of a region of interest (for example, a head, chest, an abdomen, a heart, a liver, an upper limb, a lower limb, a spine, a bone, a blood vessel), a morphological feature of the region of interest, a pixel feature (for example, a gray value), or the like. In some embodiments, the similarity degree between the feature image in the feature image database and the first feature image may be determined through a similarity algorithm. Exemplary similarity algorithm may include a mean hash algorithm, a histogram algorithm, or the like. In some embodiments, the similarity between the feature image in the feature image database and the first feature image may be determined by inputting the feature image in the feature image database and the first feature image into a trained similarity determination model.

In 430, the data processing system 110 (e.g., an information lookup module 1130) may look up the image description information and the diagnostic result information corresponding to the second feature image based on a pre-constructed knowledge graph of a field (may also be referred to as "knowledge graph") and the second feature image.

The image description information may be information for describing a feature of a region of interest. In some embodiments, the image description information may include at least one of a shape, a size, and a texture of the region of interest in an image. The diagnostic result information may be information relating to disease diagnosis of a region of interest. In some embodiments, the diagnostic result information may include a diagnostic result of a region of interest in an image.

In some embodiments, the data processing system 110 may further look up at least one of a disease, an incentive, a symptom, a medicine, and a treatment plan corresponding to the second feature image based on the pre-constructed knowledge graph of the field and the second feature image.

In some embodiments, the knowledge graph of the field may include a corresponding relationship between an image and a text. For example, the knowledge graph of the field may include a corresponding relationship between image entities, a corresponding relationship between text entities, and/or a corresponding relationship between an image entity and a text entity. The image entity may include an original image and/or a feature image. The text entity may include a description of at least one of an image, a diagnostic result, a disease, an incentive, a symptom, a medicine, and a treatment plan, or the like. As another example, the knowledge graph may include a corresponding relationship between a historical image report and an image in the historical image report.

In some embodiments, the knowledge graph of the fields may be constructed in advance. After obtaining the second feature image similar to the first feature image from the feature image database, the data processing system 110 may obtain the image description information and the diagnostic result information associated with the second feature image by looking, based on the second feature image, in the knowledge graph of the field. More descriptions regarding the knowledge graph may be found in FIGS. 5-7.

In 440, the data processing system 110 (e.g., a report generation module 1140) may generate an image report based on the target image, the image description information, and the diagnostic result information.

In some embodiments, the image report may include basic information (e.g., a name, an age, a gender, a check item) of the object, the target image, the image description information, and the diagnostic result information. In some embodiments, an image report template may be set in advance. After obtaining the image description information and the diagnostic result information, the data processing system 110 may fill the basic information of the object, the image description information, and the diagnostic result information into the image report template, so as to generate the image report.

In some embodiments, the image report may also include a description of at least one of a disease, an incentive, a symptom, a medicine, and a treatment plan, or the like. The data processing system 110 may fill the description of at least one of the disease, the incentive, the symptom, the medicine, the treatment plan, or the like, into the image report template, and then automatically generate the image report.

In some embodiments, the image report template may be stored in a storage device of the medical system 100 (e.g., the storage device 140, the storage device 220). The data processing system 110 may access the storage device in the medical system 100 to obtain the image report template.

In some embodiments, an error detection and an error correction may be performed on the generated image report of the target image according to error correction methods of FIGS. 12-22. In some embodiments, the generated image report of the target image may be unstructured data, and the generated image report of the target image may be stored according to unstructured data storage methods of FIGS. 23-27.

In the above-mentioned image report generation method, the data processing system 110 may obtain a target image and obtain the first feature image from the target image;

obtain the second feature image that matches the first feature image by looking, based on the first feature image, in the preset feature image database; look up image description information and diagnostic result information corresponding to the target image based on a preset knowledge graph of a field and the second feature image; and generate an image report based on the target image, the image description information, and the diagnostic result information. In some embodiments of the present application, the data processing system 110 may automatically generate an image report using a pre-constructed knowledge graph of a field, thereby eliminating the need for the doctor to manually fill in the image report, which improves the efficiency of image report generation.

It should be noted that the above description regarding the process 400 is merely provided for the purposes of illustration, and not intended to limit the scope of the present disclosure. For persons having ordinary skills in the art, multiple variations and modifications may be made to the process 400 under the teachings of the present disclosure. However, those variations and modifications do not depart from the scope of the present disclosure. For example, the process 400 may be executed by the user terminal 130, for example, the CPU 340 and/or GPU 330, and/or by one or more modules shown in FIG. 11.

FIG. 5 is a flowchart illustrating an exemplary process 500 for constructing a knowledge graph of a field according to some embodiments of the present disclosure. In some embodiments, the process 500 may be performed by the medical system 100 (e.g., the data processing system 110). For example, the process 500 may be performed by a server of a PACS, a post-processing workstation, a doctor workstation, or an imaging system. For example, the process 500 may be executed by the processor 210. Another example, the process 500 may be executed by one or more modules shown in FIG. 11. In some embodiments, the process 500 may be stored in a storage device (e.g., the storage device 140) in the form of a program or instruction, and the process 500 may be achieved when the medical system 100 executes the program or instruction. The operation schematic of the process 500 presented below is illustrative. In some embodiments, the process may be accomplished with one or more additional operations not described, and/or without one or more of the operations discussed. Further, an order of operation of the process 500 as below and the following description is not intended to be limiting. In some embodiments, the knowledge graph of the field illustrated in FIG. 4 may be constructed based on the process 500.

In 510, the data processing system 110 (e.g., the information lookup module 1130) may determine a graph structure of a knowledge graph of a field.

The graph structure may be used to indicate an entity type and an entity connection relationship. In some embodiments, in a knowledge graph of a medical field, as shown in Table 1, the entity type may include an image entity and/or a text entity. The image entity may include an original image and/or a feature image. The text entity may include a description of at least one of an image, a diagnostic result, a disease, an incentive, a symptom, a medicine, a treatment plan, or the like. The entity connection relationship may represent a relationship between entities, including at least one of observation, inhibitory effect, combination, alternative, use, feature, result, relating, complication, inclusion, inducing, performance, etc.

TABLE 1

| Entity Type | Attribute |
|---|---|
| Original image | ID, Generation Date, Path |
| Feature Image | ID, Lesion or not, Path |
| Diagnostic Result | ID, Name, Description |
| Image description | ID, Name, Description |
| Disease | ID, Chinese medicine name, Western medicine name, Description, Susceptible population, Infectivity |
| Incentive | ID, Name, Description, Type |
| Symptom | ID, Name, Description, Severity, Body part |
| Medicine | ID, Chinese medicine name, Western medicine name, Description |
| Treatment Plan | ID, Description, Treatment cycle |

Figure 6:
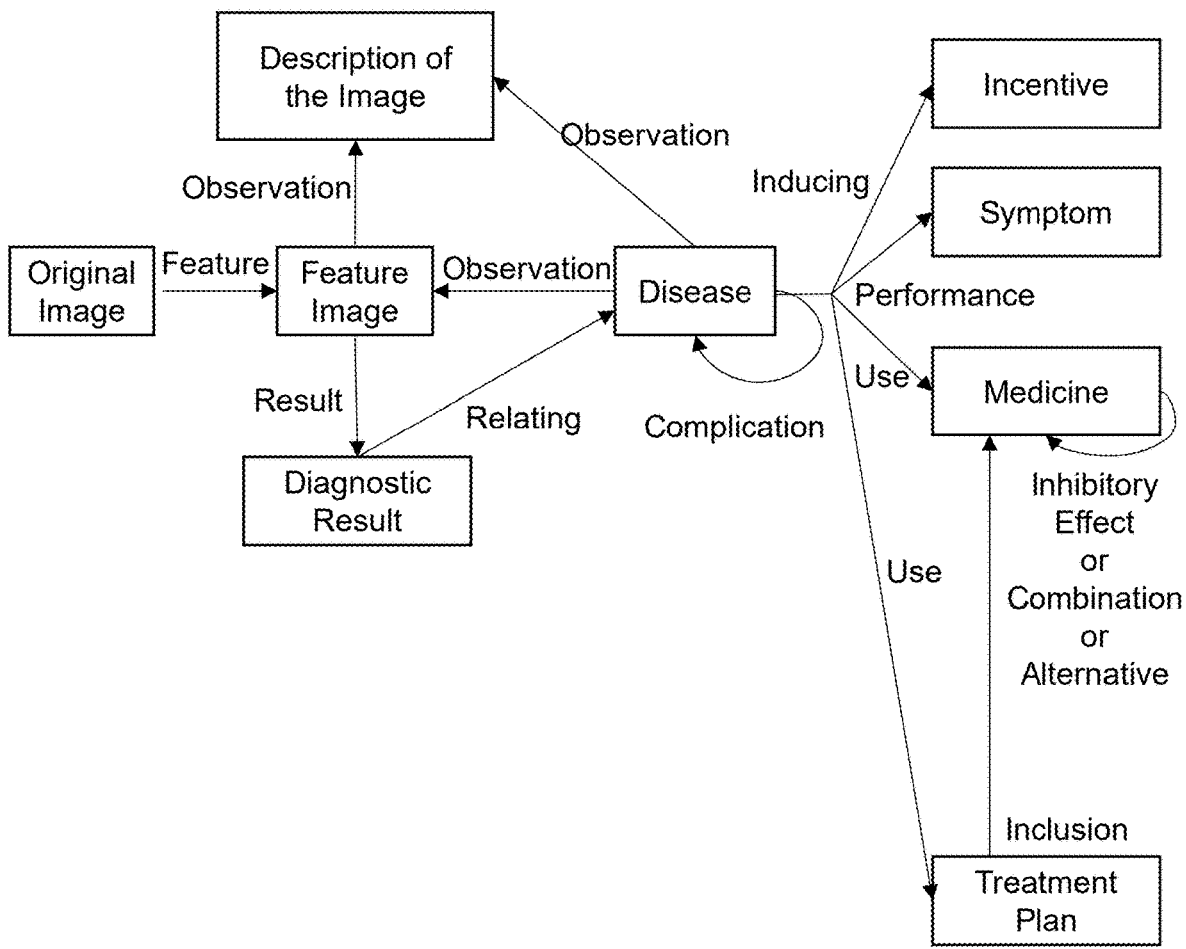
FIG. 6 is a schematic diagram illustrating an exemplary graph structure according to some embodiments of the present disclosure.

In some embodiments, after determining the entity type and the entity connection relationship, the graph structure as shown in FIG. 6 may be determined according to the above-described entity type and entity connection relationship.

As shown in FIG. 6, in the graph structure, the entity type may include an image entity and a text entity. The image entity may include the original image and/or the feature image. The text entity may include a description of the image, the diagnostic result, the disease, the incentive, the symptom, the medicine, the treatment plan, or the like. The entity connection relationship may include observation, inhibitory effect, combination, alternative, use, feature, result, relating, complication, inclusion, inducing, performance, etc. The original image and feature image may have a "feature" relationship. The feature image and image description may have an "observation" relationship. The feature image and the diagnostic result may have a "result" relationship. The feature image and the disease may have an "observation" relationship. The image description and the disease may have an "observation" relationship. The diagnostic result and the disease may have a "relating" relationship. Multiple diseases corresponding to the same feature image may have a "complication" relationship. The disease and the incentive may have an "inducing" relationship. The disease and the symptom may have a "performance" relationship. The disease and the medicine may have a "use" relationship. The disease and the treatment plan may have a "use" relationship. The treatment pan and the medicine may have an "inclusion" relationship. Multiple medicines corresponding to the same disease may have an "inhibitory effect" relationship, an "alternative" relationship, or a "combination" relationship, which represents that the multiple medicines may not be taken simultaneously, a part of the multiple medicines may be selected to be taken, or the multiple medicines may need to be taken together, respectively.

In 520, the data processing system 110 (e.g., information lookup module 1130) may obtain an original text and an original image of a preset field, extract entity data from the original text and the original image, and determine an association relation among the entity data.

In some embodiments, the preset field may include a medical field. In some embodiments, the data processing system 110 may obtain the original text and the original image through various methods including at least one of: obtaining an original text of medical common sense from books, newspapers, and websites; obtaining an original text and an original image relating to diagnosis from electronic medical records, test reports, diagnostic reports; obtaining an original image from a medical imaging device. The present disclosure embodiment does not limit the obtaining method.

In some embodiments, the data processing system 110 may store the acquired original text into a MySQL data table, store the obtained original image in the DICOM format into an image database (for example, the PACS, the storage device 140, the storage device 220), and store a save path into the MySQL data table.

In some embodiments, the obtained original text may undergo an error correction, and then, be stored. In some embodiments, the obtained original text may be used as a text to be processed, and may be corrected based on text error correction methods of FIGS. 12-22.

In some embodiments, the original text and original image obtained from the books, the newspapers, the websites, the electronic medical records, the test reports, the diagnostic reports, etc., may be unstructured data, which may be stored according to unstructured data storage methods of FIGS. 23-27.

In some embodiments, after the data processing system 110 obtains the original text and the original image, text entity data may be extracted from the original text, and an association relation between the extracted text entity data may be determined. Image entity data may also be extracted from the original image, and then, an association relation between the original image and the image entity data may be determined. The text entity data and the image entity data may also be extracted from the original text and the original image, and then, an association relation between the text entity data and the image entity data may be determined.

In 530, the data processing system 110 (e.g., the information lookup module 1130) may construct the knowledge graph of the preset field based on the graph structure, the entity data, and the association relation among the entity data.

In some embodiments, after determining the graph structure, entity data, and the association relation among the entity data, the data processing system 110 may divide the entity data into a plurality of triads based on the association relation among the entity data, and then generate the knowledge graph by filling the plurality of triads into the graph structure. For example, the knowledge graph may be generated by storing multiple triads in a preset graph database.

Figure 7:
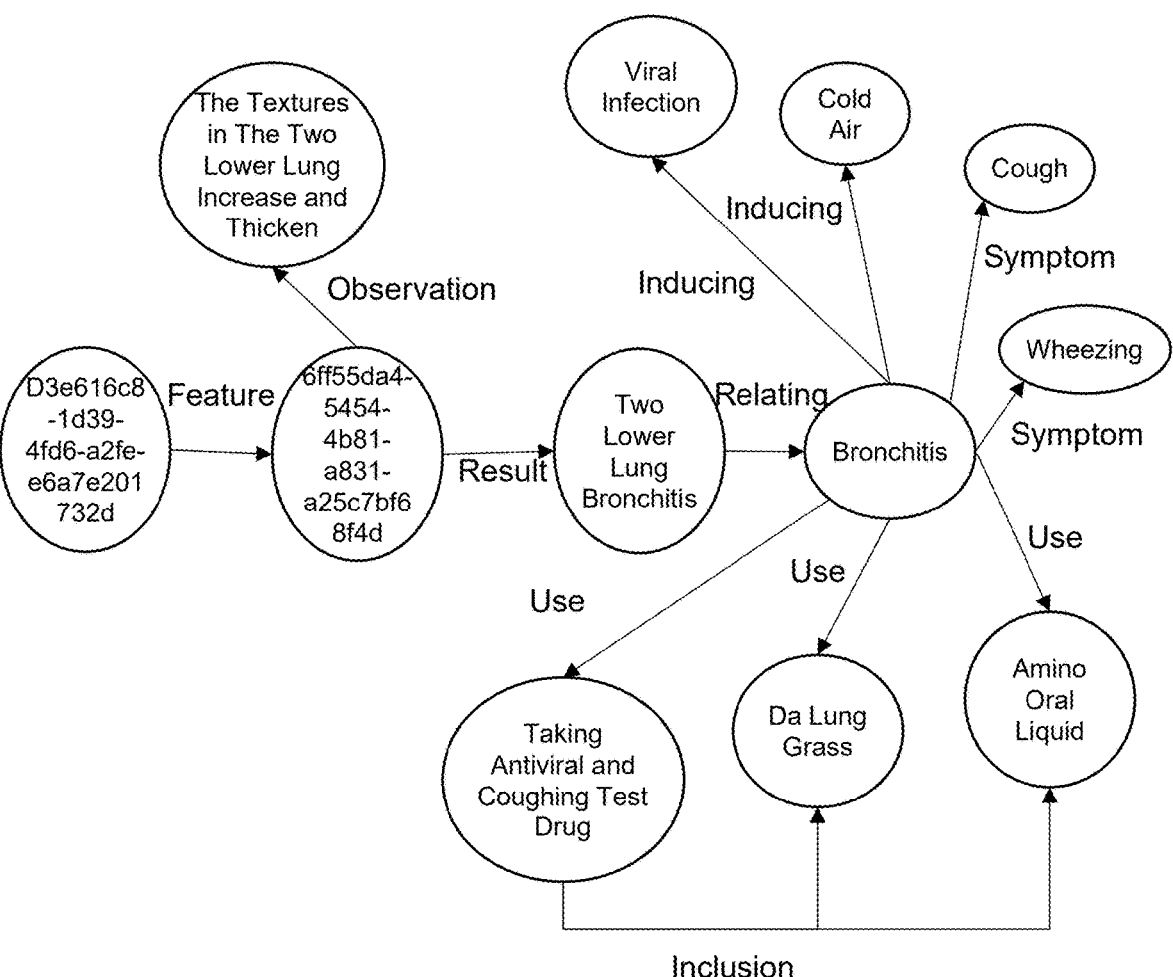
FIG. 7 is a schematic diagram illustrating an exemplary knowledge graph of a field according to some embodiments of the present disclosure.

For example, in a triad format of <entity, relationship, entity>, the association relation among text entity data may be represented as <XX pneumonia (disease), use, methylprednisolone (drug)>, the association relation between the text entity data and the image entity data may be represented as <XX pneumonia (disease), observation, 6ff55da4-5454-4b81-a831-a25c7bf68f4d (feature image)>, and the association relation among the image entity data may be represented as <d3e616c8-1d39-4fd6-a2fe-*e*6a7e201732d (original image), feature, 6ff55da4-5454-4b81-a831-a25c7bf68f4d (feature image)>. d3e616c8-1d39-4fd6-a2fe-e6a7e201732d may be a unique identifier of a certain original image, and 6ff55da4-5454-4b81-a831-a25c7bf68f4d may be a unique identifier of the feature image of the original image. Thereafter, the above triad(s) may be stored in an Neo4j image database, and the knowledge graph of the field may be obtained, as shown in FIG. 7. The present disclosure embodiment does not limit the graph database.

As shown in FIG. 7, the original image d3e616c8-1d39-4fd6-a2fe-*e*6a7e201732d may correspond to the feature image 6ff55da4-5454-4b81-a831-a25c7bf68f4d. The image description of the feature image may be "the textures in the two lower lung increase and thicken," the diagnostic result may be "two lower lung bronchitis," the corresponding disease may be "bronchitis." An incentive of the bronchitis is "viral infection" and/or "cold air," the symptom is "cough" and/or "wheezing," the treatment plan is "taking antiviral and coughing test drug," and the medicine is "Da Lung grass" and/or "amino oral liquid," wherein the "taking antiviral and coughing test drug" includes the medicine "Da Lung Cao" and/or "amino oral liquid."

In the above embodiments, the data processing system 110 may determine the graph structure of the knowledge graph of the field, obtain the original text and original images of a preset field, extract entity data from the original text and the original image, determine the association relation among the entity data, and construct the knowledge graph of the preset field based on the graph structure, the entity data, and the association relation among the entity data. In the prior art, the knowledge graph may usually include only text. The present disclosure provides a multimode knowledge graph of the field according to the text and the image. Compared with the prior art, the knowledge graph of the field provided in the present disclosure is more comprehensive and more accurate.

In some embodiments, entity data may be extracted from the original text and the original image, and the operation for determining the association relation among entity data may include implementing the following manner.

One of the entity data extraction methods may include: for the original text, inputting the original text into a trained word segmentation model; obtaining a plurality of word segmentation results outputted by the trained word segmentation model; inputting the plurality of word segmentation results into a trained entity identification model; obtaining a feature text outputted by the trained entity identification model; and determining the feature text as the entity data. For example, an original text may include an image description, a diagnostic result, and a disease type. The original text may be input into the trained word segmentation model and the entity identification model to obtain feature texts corresponding to the image description, the diagnostic result, and the disease type, respectively. The feature texts may include a description of the attributes of the text entity in Table 1.

The word segmentation model and the entity identification model may be trained by a terminal itself, or may be trained by a server, and the terminal may obtain the model(s) from the server. The present disclosure does not limit this.

In some embodiments, a training process of the word segmentation model may include: using a hot word mining way to extract common words and corresponding standard expressions from massive texts; generating a synonym table based on a verification result of the common words and the corresponding standard expressions obtained by verifiers; converting the synonym table into a word segmentation dictionary; and then using the word segmentation dictionary and artificially annotated word segmentation data as an input to train the word segmentation model.

In some embodiments, the original text may be input into the word segmentation model. After obtaining a plurality of word segmentation results outputted by the word segmentation model, the data processing system 110 may perform N-Gram (N=2, 3, 4 . . . ) frequency statistics, and display one or more N-Gram results of which a count is K with higher frequency. Next, the data processing system 110 may receive verification information inputted by a verification personnel for the K N-Gram results with higher frequency, and determine whether each N-Gram result needs to be merged into a vocabulary according to the verification information, and then, the vocabulary is updated to the word segmentation dictionary. For example, an original text "renal arcuate arteries radiate at regular intervals" is segmented by the word segmentation model, and the word segmentation result is "renal, arcuate, arteries, radiate, at, regular, intervals," from which multiple 3-Grams may be obtained, {"renal, arcuate, arteries," "arcuate, arteries, radiate," "arteries, radiate, at," "radiate, at, regular," "at, regular, intervals" }. Through an artificially confirm that "renal, arcuate, arteries" is a professional term, "renal, arcuate, arteries" may be merged into "renal arcuate arteries" and added to the word segmentation dictionary. After that, the word segmentation model may be retrained according to the updated word segmentation dictionary. Through the N-Gram frequency statistics and artificial verification of the word segmentation result, a long professional vocabulary in the medical field may be avoided from being segmented.

In some embodiments, a training process of the entity identification model may include: obtaining a training sample set, and generating the entity identification model by training a model based on the training sample set. The entity recognition model may use a Word2Vec+BiLSTM+CR structure. The structure of the entity identification model is not limited.

In some embodiments, the association relation determination method corresponding to the above-described entity data extraction method may include: inputting the original text and a plurality of feature texts into a trained relation extraction model, and obtaining the association relation among the plurality of feature texts.

In some embodiments, the relation extraction model may be trained by a terminal itself, or may be trained by a server, and the terminal may obtain the model(s) from the server. The present disclosure does not limit this.

In some embodiments, the data processing system 110 may input the original text and the above-mentioned plurality of feature texts into the relation extraction model. The relation extraction model may determine an association relation among the plurality of feature texts according to the content of the original text, and output the association relation. The above relation extraction model may use a Gated Recurrent Unit (GRU) model, and the present disclosure embodiments do not limit a structure of the relation extraction model.

It will be appreciated that, by using the trained word segmentation model, the trained entity identification model, and the trained relation extraction model, the data processing system 110 may quickly and accurately extract the text entity data from the original text and determine the relation among the text entity data, which provides a large amount of textual basis for constructing the knowledge graph of the field.

Another entity data extraction method may include: for the original image, inputting the original image into a trained identification model; obtaining an identification result outputted by the identification model; obtaining a feature image of the region of interest in the original image; and determining the feature image of the region of interest as the entity data.

The identification result may be used to indicate a region of interest in the original image. For example, the identification model may use a neural network model. After inputting the original image into the neural network model, the neural network model may output the original image having a region identification box representing the region of interest. Next, the data processing system 110 may segment the feature image in the region identification box as the entity data. A structure of the identification model is not limited to the embodiments of the present disclosure.

In some embodiments, the association relation determination method corresponding to the above-described entity data extraction method may include storing the feature image into a feature image database, and storing the association between the feature image and the original image into a preset data table.

In some embodiments, after segmenting the feature image from the original image, the feature image may be stored in the preset feature image database, and the association relation of "original image-feature image" may be established. Thereafter, the association relation may be stored in the MySQL data table. The structure of the data table is not limited to the embodiments of the present disclosure.

It will be appreciated that, by using the trained identification model, the data processing system 110 may quickly and accurately obtain the image entity data and determine the association relation between the image entity data and the original image, which provides a large amount of image basis for constructing the knowledge graph of the field.

Another entity data extraction method may include: extracting at least one of the image description, the diagnostic result, the disease, the incentive, the symptom, the medicine, the treatment plan, or the like, from the original text; determining the extracted data as the entity data; extracting the feature image from the original image; and determining the feature image as the entity data.

Taking the image description and the diagnostic result as an example, for original data including both the original text and the original image, for example, an electronic medical record, a diagnostic report, an image report, the data processing system 110 may obtain a plurality of feature images $P=\{p_1, p_2, \ldots, p_n\}$ by identifying the original image, wherein $p_n$ represents one feature image. The data processing system 110 may obtain a plurality of image description texts $Q=\{q_1, q_2, \ldots, q_k\}$ and a plurality of diagnostic result texts $S=\{s_1, s_2, \ldots, s_m\}$ by segmenting the original text. Each of the aforementioned feature image, the image description text, and the diagnostic result may be the entity data.

In some embodiments, the association relation determination method corresponding to the above entity extraction method may include establishing a relationship among the feature image, the image description text, and the diagnostic results text.

In some embodiments, the data processing system 110 may store the image description text and the diagnostic result text into the MySQL data table, store the feature image into the feature image database, and store a save path to the MySQL data table. Thereafter, the association relation "feature image-[observation]-image description text" may be established and expressed as $g(p_i)=q_j$, which indicates that an $i^{th}$ feature image corresponds to a $j^{th}$ image description text. In some embodiments, the association relation "feature image-[result]-diagnostic result text" may be established and expressed as $g(p_i)=s_j$, which indicates that an $i^{th}$ feature image corresponds to a $j^{th}$ diagnostic result text. The above-mentioned association relations may be stored in the MySQL data table.

In some embodiments, a unique identifier of the feature image may be generated when the feature image is stored in the feature image database. The establishment of the association relation between the feature image and the image description text and the diagnostic text may use the unique identifier of the feature image.

It will be appreciated that the data processing system 110 extracts the entity data from the original text and the original image, which provides a large number of text basic and image basic for constructing the knowledge graphs of the field, thereby making the knowledge graph of the field more comprehensive and more accurate.

In some embodiments, the data processing system 110 may generate an image-text corresponding relationship based on historical image reports. The data processing system 110 may automatically generate an image report according to the target image and the image-text corresponding relationship. In some embodiments, the data processing system 110 may identify an historical image report (for example, using an image identification model), obtain a feature image of an image in the historical image report, and store the feature image in the feature image database. The data processing system 110 may establish a corresponding relationship between the feature image and the historical image report, and store the corresponding relationship in the database. When generating an image report of the target image, the data processing system 110 may look up the second feature image that matches the first feature image in the feature image database, and then find the historical image report corresponding to the second feature image through the corresponding relationship between the feature image and the historical image report. Since the image report(s) uses a same template, the data processing system 110 may generate an image report of the target image by filling the target image and basic information of a patient corresponding to the target image in a corresponding position of the historical image report.

It should be noted that the above description is merely provided for the purposes of example and illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the process 500 may be executed by the user terminal 130, for example, the CPU 340 and/or GPU 330, and/or by one or more modules shown in FIG. 11.

FIG. 8 is a flowchart illustrating an exemplary process 800 for obtaining image description information and diagnostic result information corresponding to a target image according to some embodiments of the present disclosure. In some embodiments, the process 800 may be performed by the medical system 100 (e.g., the data processing system 110). For example, the process 800 may be performed by a server of a PACS, a post-processing workstation, a doctor workstation, or the imaging system. Another example, the process 800 may be executed by the processor 210. Another example, the process 800 may be performed by one or more modules shown in FIG. 11. In some embodiments, the process 800 may be stored in a storage device (e.g., the storage device 140) in the form of a program or instruction, and the process 800 may be achieved when the medical system 100 executes the program or instruction. The operation schematic of the process 800 presented below is illustrative. In some embodiments, the process may be accomplished with one or more additional operations not described, and/or without one or more of the operations discussed. In addition, an order of operation of the process 800 as below and the following description is not intended to be limiting.

As shown in FIG. 8, the above-mentioned operation for looking up the image description information and the diagnostic result information corresponding to the second feature image based on the knowledge graph of the field and the target image may include following operations.

In 810, the data processing system 110 (e.g., the information lookup module 1130) may look up a second feature image in a knowledge graph of a field, and obtain an image description set and a diagnostic result set corresponding to the second feature image.

In some embodiments, the image description set may include a plurality of image description texts, and the diagnostic result set may include a plurality of diagnostic result texts.

In some embodiments, the data processing system 110 may segment a first feature image from a target image, and obtain the second feature image that matches the first feature image by looking, based on the first feature image, in a preset feature image database. A number (or count) of the second feature image may be one or more. After that, the data processing system 110 may look up the second feature image in the knowledge graph of the field. A number (or count) of the image description text and the diagnostic result text corresponding to each second feature image may be one or more. In this way, a plurality of image description texts and diagnostic result texts may be obtained. Then, the plurality of image description texts may be combined into the image description set, and the plurality of diagnostic result texts may be combined into the diagnostic result set.

In 820, the data processing system 110 (e.g., the information lookup module 1130) may obtain a deduplicated image description text and a deduplicated diagnostic result text by performing a de-duplication on the image description set and the diagnostic result set, and determine the image description information and diagnostic result information based on the deduplicated image description text and the deduplicated diagnostic result text.

In some embodiments, since the image description set includes a plurality of image description texts, the image description texts may have repeated descriptions. Therefore, the image description set may need to be deduplicated. Similarly, the diagnostic result set may also need to be deduplicated. A process of de-duplication may include: segmenting an image description text to obtain a word segmentation result; determining whether the de-duplication segmentation result includes a text content of another image description text, and if so, the another image description text may be removed. The de-duplication of the diagnostic result texts may be similar to the above process, which is not limited in the embodiment of the present disclosure.

In some embodiments, after the de-deduplication, the deduplicated image description text and the deduplicated diagnostic result text may be obtained. The deduplicated image description text and the deduplicated diagnostic result text may be arranged in a certain order, thereby obtaining the image description information and the diagnostic results information.

In the abovementioned process for looking up the image description information and the diagnostic result information corresponding to the target image based on the pre-constructed knowledge graph of the field and the second feature image, the data processing system 110 may look up the second feature image in the knowledge graph of the field; obtain an image description set and a diagnostic result set corresponding to the second feature image; obtain the deduplicated image description text and the deduplicated diagnostic result text by performing a de-duplication on the image description set and the diagnostic result set; determine the image description information and the diagnostic result information based on the deduplicated image description text and the deduplicated diagnostic result text. In some embodiments of the present disclosure, the data processing system 110 may use the knowledge graph of the field to look up the image description information and the diagnostic result information. Since the knowledge graph of the field is a multi-modal knowledge graph including texts and images, more comprehensive and accurate image descriptive information and diagnostic result information may be found. In addition, the data processing system 110 may de-duplicate the searched image description set and diagnostic result set, which may avoid duplicate descriptions in the image report and make the image report more concise.

It should be noted that the above description is merely provided for the purposes of example and illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the process 800 may be executed by the user terminal 130, for example, the CPU 340 and/or GPU 330, and/or by one or more modules shown in FIG. 11.

FIG. 9 is a flowchart illustrating an exemplary process 900 for generating an image report according to some embodiments of the present disclosure. In some embodiments, the process 900 may be performed by a medical system 100 (e.g., data processing system 110). For example, the process 900 may be performed by a server of a PACS, a post-processing workstation, a doctor workstation, or the imaging system. For example, the process 900 may be executed by the processor 210. Another example, the process 900 may be performed by one or more modules shown in FIG. 11. In some embodiments, the process 900 may be stored in the storage device (e.g., the storage device 140) in the form of a program or instruction, and the process 900 may be achieved when the medical system 100 executes the program or instruction. The operation schematic of the process 900 presented below is illustrative. In some embodiments, the process may be accomplished with one or more additional operations not described, and/or without one or more of the operations discussed. In addition, an order of operation of the process 900 as below and the following description is not intended to be limiting.

As shown in FIG. 9, the process 900 may include the following operations.

In 910, the data processing system 110 (e.g., the information lookup module 1130) may look up disease information, incentive information, symptom information, medicine information, and treatment plan information corresponding to a second feature image based on a knowledge graph of a field of a preset field and the second feature image.

In some embodiments, in the knowledge graph of the field, what is associated with the second feature image may also include disease information. Disease-related incentive information, symptom information, treatment plan information, and medicine information may be obtained through an association query and reasoning based on the disease information, as shown in FIG. 7. Therefore, after the image description text and the diagnostic result associated with the second feature image are found in the knowledge graph of the field, the disease information, the incentive information, the symptom information, the treatment plan information, and the medicine information associated with the second feature image may be further found. Understandably, the disease information, the incentive information, the symptom information, the treatment plan information, and the medicine information associated with the second feature image may be used as the disease information, the incentive information, the symptom information, the treatment plan information, and the medicine information corresponding to the target image.

In 920, the data processing system 110 (e.g., the report generation module 1140) may generate an image report of the target image based on the target image, the disease information, the incentive information, the symptom information, the medicine information, and the treatment plan information.

In some embodiments, the data processing system 110 may preset an image report template in advance, and fill the disease information, the incentive information, the symptom information, the medicine information, and the treatment plan information into corresponding locations in the image report template after obtaining these information, thereby automatically generating the image report.

For example, the data processing system 110 may obtain an image report template, as shown in FIG. 10, and the image report template may include a patient basic information module 1010, an image description module 1020, and a diagnostic result module 1030. After obtaining the image description and the diagnostic result corresponding to the target image, the data processing system 110 may fill these information to the corresponding module of the image report template, and automatically generate an image report, such as the image report 1000 shown in FIG. 10.

In the above embodiments, the data processing system 110 may look up the disease information, the incentive information, the symptom information, the treatment plan information, and the medicine information corresponding to the target image based on the pre-constructed knowledge graph of the field and the second feature image; and generate an image report of the target image based on the target image, the disease information, the incentive information, the symptom information, the medicine information, and the treatment plan information. In some embodiments of the present disclosure, the knowledge graph of the field may not only include a feature image, an image description text, and a diagnostic result text, and may also include the disease information, the incentive information, the symptom information, the medicine information, and the treatment plan information. Therefore, compared with the prior art, the present disclosure examples combine the intelligent query and reasoning of the knowledge graph to enrich a content of the image report, which may provide more and more comprehensive information support for a doctor.

It should be noted that the above description is merely provided for the purposes of example and illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the process 900 may be executed by the user terminal 130, for example, the CPU 340 and/or GPU 330, and/or by one or more modules shown in FIG. 11.

FIG. 11 is a block diagram illustrating an exemplary image report generation device according to some embodiments of the present disclosure. In some embodiments, the hardware and/or software of the data processing system 110 and/or the user terminal 130 may be implemented based on the image report generating device 1100. In some embodiments, the image report generation device 1100 may include an image obtaining module 1110, an image lookup module 1120, an information lookup module 1130, and a report generation module 1140.

The image obtaining module 1110 may be configured to obtain a target image, and obtain a first feature image from the target image, wherein the first feature image may be an image of a region of interest of the target image.

The image lookup module 1120 may be configured to obtain a second feature image that matches the first feature image by looking, based on the first feature image, in a preset feature image database.

The information lookup module 1130 may be configured to look up, based on a pre-constructed knowledge graph of a field and the second feature image, text information corresponding to the second feature image, for example, at least one a description of image description information, diagnostic result information, a disease, an incentive, a symptom, a medicine, and a treatment plan. In some embodiments, the information lookup module 1130 may include a first information lookup module configured to look up the image description information and the diagnostic result information corresponding to the second feature image based on the pre-constructed knowledge graph of the field and the second feature image.

The report generation module 1140 may be configured to generate an image report of the target image. The report generation module 1140 may include a first report generation module configured to generate an image report based on the target image, the image description information, and the diagnostic results information.

In one embodiment, the information lookup module 1130 may also include:

a structure determination module configured to determine a graph structure of the knowledge graph of the field, and the graph structure may include an entity type and an entity connection relationship;

a data and relation extraction module configured to obtain an original text and original image of a preset field, extract entity data from the original text and the original image, and determine the association relation between among entity data.

a graph construction module configured to construct the knowledge graph of the preset field based on the graph structure, the entity data, and the association relation among the entity data.

In some embodiments, the entity type may include at least one of an original image, a feature image, an image description, a diagnostic result, a disease, an incentive, a symptom, a medicine, or a treatment plan.

In some embodiments, the entity connection relationship may include at least one of observation, inhibitory effect, combination, alternative, use, feature, result, relating, complication, inclusion, inducing, performance, or the like.

In some embodiments, for the original text, the above data and relation extraction modules may be specifically used to input the original text into a trained word segmentation model; obtain a plurality of word segmentation results outputted by the trained word segmentation model; input the plurality of word segmentation results into a trained entity identification model; obtain a feature text outputted by the trained entity identification model; and determine the feature text as the entity data.

In some embodiments, the above data and relation extraction modules may be specifically configured to input the original text and multiple feature text into a trained relation extraction model, and obtain the association relation among the plurality of feature texts.

In some embodiments, the data and relation extraction module may be specifically configured to input the original image into a trained identification model, and obtain an identification result outputted by the identification model. The identification result may be configured to indicate a region of interest in the original image. A feature image of the region of interest may be obtained in the original image. The feature image of the region of interest may be determined as the entity data.

In some embodiments, the image report generation device 1100 may also include:

an image storage module configured to store the feature image into the feature image database and store the association relation between the feature image and the original image into a preset data table.

In some embodiments, the above data and relation extraction module may be specifically configured to extract the image description text and the diagnostic result text corresponding to the original image from the original text; determine the image description text and diagnostic results text as the entity data; extract the feature image from the original image and determine the feature image as the entity data; and construct an association relation between the feature image of the original image and the image description text and the diagnostic result text.

In some embodiments, the above-described graph construction module may be specifically used to combine entity data into a plurality of triads based on the association relation among the entity data; and generate the knowledge graph of the field by storing the plurality of triads into a preset graph database.

In some embodiments, the first information lookup module may be specifically configured to look up the second feature image in the knowledge graph of the field; obtain the image description set and the diagnostic result set corresponding to the second feature image, the image description set including a plurality of image description texts, and the diagnostic result set including a plurality of diagnostic result texts; obtain a deduplicated image description text and a deduplicated diagnostic result text by performing a deduplication on the image description set and the diagnostic result set; and determine the image description information and diagnostic result information based on the deduplicated image description text and the deduplicated diagnostic result text.

In some embodiments, the image lookup module 1120 may be specifically configured to determine a similarity degree between the first feature image and each feature in the feature image database, thereby determining a plurality of similarity degrees; and determine a feature image in the feature image database that satisfies a preset condition as the second feature image.

In some embodiments, the information lookup module 1130 may also include a second information lookup module configured to look up disease information, incentive information, symptom information, treatment plan information, and medicine information corresponding to the target image based on the pre-constructed knowledge graph of the field and the second feature image.

In some embodiments, the report generation module 1140 may also include a second report generation module configured to generate an image report based on the target image, the image description information, the diagnostic result information, the disease information, the incentive information, the symptom information, the treatment plan information, and the medicine information.

The specific limitation regarding the image report generation device 1100 may be found in above-mentioned limitation of the image report generation method (e.g., the process 400, the process 500, the process 800, the process 900), and details are not repeated herein. Each module in the above-described image report generation device 1100 may be implemented through software, hardware, and a combination thereof. The above modules may be embedded in or independent from a processor in a computing device, and may also be stored in a storage device of the computing device in a software form, so that the processor may call and execute the operations corresponding to each of the above modules.

It should be noted that the above description is merely provided for the purposes of example and illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the present disclosure provides a computer readable storage medium that stores a computer program. When the computer program is executed by a processor (e.g., the data processing system 110, the user terminal 130, the processor 210, the CPU 340, the GPU 330, or one or more modules of FIG. 11), at least one of the process 400, the process 500, the process 800, and the process 900 may be implemented.

With the popularization and application of medical information systems in a medical industry, most medical institutions may use medical information systems to store and compile medical data, for example, test reports, image reports, or diagnostic reports. While, medical texts occupies a large proportion of medical data, and how to check wrong medical text data is a very important work. At present, there are many ways to check the wrong medical text data, mainly including: using a detection model having a function of detecting a wrong text to detect the wrong text, and then manually modifying the wrong text to obtain corrected medical text data. However, the above-mentioned correction method may result in an inaccurate correction. In view of the technical problem, the present disclosure provides systems and methods that may effectively improve the accuracy and efficiency of error correction on medical texts.

FIG. 12A is a flowchart illustrating an exemplary text correction process 1200 according to some embodiments of the present disclosure. In some embodiments, the process 1200 may be implemented in the medical system 100 (e.g., the data processing system 110). For example, the process 1200 may be executed by a server of a medical system. Exemplary medical systems may include a picture archiving and communication systems (PACS), a post-processing workstation, a surgical system, a hospital information system (HIS), a laboratory information management system (LIS), a radiology information system (RIS), a doctor workstation, a nurse workstation, an imaging system, a hospitalization management system, a door agency management system, or a charging system. For example, the process 1200 may be executed by the processor 210. As another example, the process 1200 can be executed by one or more modules illustrated in FIG. 22. In some embodiments, the process 1200 may be stored in a storage medium (e.g., the storage device 140) as a form of instructions or programs, and the process 1200 may be implemented when the instructions or programs are executed by the medical system 100. The operations of the illustrated process 1200 presented below are intended to be illustrative. In some embodiments, the process 1200 may be accomplished with one or more additional operations not described, and/or without one or more of the operations discussed. Additionally, the order in which the operations of the process 1200 as illustrated in FIG. 12A and described below is not intended to be limiting.

In 1210, the data processing system 110 may obtain a type and a location of an error text by performing an error detection on a text to be processed.

In some embodiments, the text to be processed may be a text waiting for an error detection and error correction. A computer device may obtain the text to be processed from an HIS, an RIS, an electronic medical record system, a speech recognition result text system, a question-and-answer system, or other systems. The type of the error text may include a type of wrong word, a type of absence, a type of disorder, or a type of redundancy. The location of the error text may represent a location where the error text is in the text to be processed. A text may include at least one of symbols, numbers, letters, characters, words, phrases, sentences.

Error detection may include detecting whether an error text is included in the text to be processed, and/or determining the type and location of the error text. In some embodiments, the computer device (e.g., the data processing system 110) may input the text to be processed into a trained error detection model for performing an error detection to obtain the type of error text included in the text to be processed and the location of the error text in the text to be processed. The error detection model may be a neural network model or a machine learning model. For example, the BiLSTM-CRF model may be widely used because of its own error detection function, and the present disclosure does not limit the selection of the error detection model.

For example, the present disclosure provides a method of training the BiLSTM-CRF model. The method may include: labeling a type and location of the error text in each sample text using a preset sequence labeling method to obtain labeled text; the labeled text being used as a training sample and input into an initial BiLSTM-CRF model for training to obtain a trained BiLSTM-CRF model. The training BilSTM-CRF model may output the type and the location of an error text in text to be processed by inputting a text to be processed. It should be noted that the above sequence labeling method may be any type of labeling method, such as a Bio sequence labeling or Bioes sequence labeling.

Figure 12B:
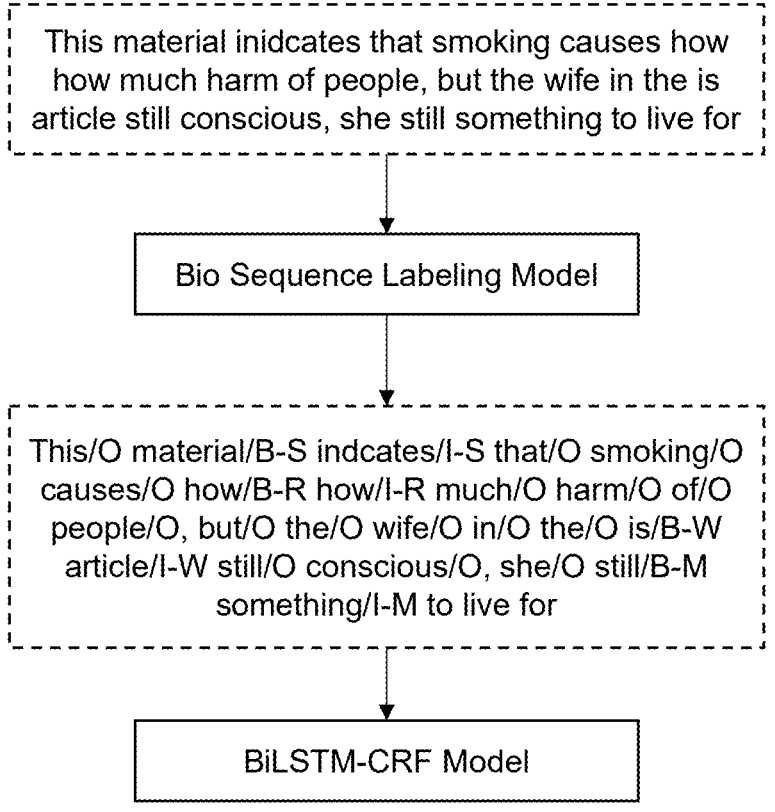
FIG. 12B is a flowchart illustrating an exemplary training process according to some embodiments of the present disclosure.

For example, as shown in FIG. 12B, the sample text is "this material indicates that smoking causes how much harm of people, but the wife in the is article still conscious, she still something to live for." The text to be processed may be input into the Bio sequence labeling model for labeling. The labeled sample text may be "this/O material/B-S indicates/I-S that/O smoking/O causes/O how/B-R how/I-R much/O harm/O of/O people/O, but/O the/O wife/O in/O the/O is/B-W article/I-W still/O conscious/O, she/O still/B-M something/I-M to live for". Where R represents a type of redundancy, M represents a type of absence, S represents a type of wrong word, W represents a type of disorder, B represents the beginning of the error text, I represents the internal of the error text, and O represents the outside of the error text. The label symbol may be set by the computer device, which is not limited here. After the labeled sample text is obtained, the computer device may determine the labeled sample text as a training sample text and input the training sample into the BiLSTM-CRF model to train.

In 1220, the data processing system 110 may determine a target error correction strategy corresponding to the type of the error text based on a corresponding relationship between the type of the error text and the target error correction strategy.

In some embodiments, the error correction strategy may be an approach for correcting an error text. The corresponding relationship between the type of the error text and an error correction strategy may be stored in a database.

In some embodiments, when the type of error text is obtained based on the aforementioned operations, the computer device may determine the target error correction strategy corresponding to the type of the error text according to the type of the error text and the corresponding relationship between the type of the error text and the error correction strategy, so that the error text of the corresponding type may be corrected in the future according to the error correction approach indicated by target error correction strategy. For example, if the type of error text is the type of wrong word, the corresponding target error correction strategy may include a pronunciation comparison error correction strategy and/or a similarity comparison error correction strategy. If the type of error text is the type of absence or the type of disorder, the corresponding target error correction strategy may include a matching degree comparison error correction strategy. If the type of error text is the redundancy type, the corresponding target error correction strategy may include a deleting error correction strategy.

In 1230, the data processing system 110 may perform an error correction on the error text based on the target error correction strategy and the location of the error text.

In some embodiments, after the target error correction strategy corresponding to the type of error text is determined, the computer device may find the error text or a text relating to the error text in the text to be processed according to the location of the error text using the approach indicated by the target error correction strategy. The error text or the text relating to the error text may be performed some error correction operations, such as an adding operation, a deleting operation, a removing operation, a modifying operation, etc., to obtain the corrected text.

According to data processing method described in the present disclosure, the type and the location of the error text may be obtained by performing an error detection on a text to be processed, the target error correction strategy corresponding to the type of the error text may be determined based on the corresponding relationship between the type of the error text and the error correction strategy, and the error correction on the error text may be performed based on the target error correction strategy and the location of the error text. In this way, since each type of error text corresponds to a target error correction strategy, error correction for each type of error text may be implemented. Compared with conventional data processing method using a database to obtain the text for error correction for all types of error texts, which may need to perform amount of data processing and have a low accuracy, the error correction method described in the present disclosure may improve the accuracy of error correction and data processing efficiency.

In some embodiments, when the type of error text includes at least one of the type of wrong word, the type of absence, and the type of disorder, an implementation of the operation 1230 may be provided. As shown in FIG. 13, the operation 1230 "performing an error correction on the error text based on the target error correction strategy and the location of the error text," may include the following operations.

In 1310, the data processing system 110 may determine at least one candidate text corresponding to the error text based on the target error correction strategy and the location of the error text.

In some embodiments, when the type of error text includes the type of wrong word, the computer device may determine at least one candidate text corresponding to the error text by comparing the error text with a plurality of preset texts. In some embodiments, the computer device may also determine at least one candidate text corresponding to the error text by comparing the similarity between the error text and a plurality of preset texts. When the type of error text includes the type of absence or the type of disorder, the computer device may determine at least one candidate text corresponding to the error text by comparing a matching degree between the error text and a plurality of preset texts.

In some embodiments, a similarity between an error text and a preset text or a matching degree between an error text and a preset text may be determined based on at least one of readings, spellings, words, semantics, contexts of the error text and the preset text. In some embodiments, the preset text may be determined as a candidate text if the similarity or the matching degree between the error text and a preset text is greater than a threshold (e.g., 30%, 40%, 50%, 60%, 70%, 80%, 90%, 95%, etc.).

In 1320, the data processing system 110 may perform an error correction on the error text based on the at least one candidate text.

When at least one candidate text is obtained based on the above operations, the computer device may perform an error correction on the error text using one of the at least one of candidate text. In some embodiments, the computer device may select one candidate text from the at least one of candidate text according to a preset rule and replace the error text with the selected candidate text, or add the selected candidate text to the corresponding position in the text to be processed to perform the error correction on the error text. The preset rule may be determined by the computer device according to actual needs. For example, the preset rule may include selecting at least one candidate text with a highest similarity or a highest matching degree.

According to the above error correction data processing method, error correction for the type of wrong word, the type of absence, and the type of disorder may be implemented and each type of error text may correspond to a target error correction strategy. The computer device may perform the corresponding error correction operation according to the type of error text, which may improve the accuracy of the error correction.

In some embodiments, when the type of error text includes the type of wrong word, as shown in FIG. 14, the operation 1310 "determining at least one candidate text corresponding to the error text based on the target error correction strategy and the location of the error text" may include the following operations.

In 1410, the data processing system 110 may extract a text of the type of wrong word from the text to be processed based on a location of the text of the type of wrong word.

In some embodiments, when the type of error text detected by the computer device is the type of wrong word, the text of the type of wrong word may be determined and extracted from the text to be processed according to the location of the text of the type of wrong word, so that the text of the type of wrong word may be used for later retrieval.

In 1420, the data processing system 110 may select, from a first database, a text that is a homophone with the text of the type of wrong word, and/or, a text having a similarity to the text of the type of wrong word greater than a similarity threshold, as the candidate text.

In some embodiments, the first database may include any type of database. The preset similarity threshold may be determined by the computer device in advance according to an error correction accuracy. Specifically, when the text of the type of wrong word is obtained, the computer device may determine the text of the type of wrong word of the type of wrong word as a target text and retrieve a text that is a homophone with the target text in the first database. The computer device may determine the retrieved text that is a homophone with the target text as the candidate text. In some embodiments, the computer device may retrieve a text that is a homophone with the target text in the first database and determine the retrieved text that is a homophone with the target text as the candidate text. In some embodiments, the computer device may calculate the similarity between the target text and each text in the first database, and determine a text having a similarity to the target text greater than the similarity threshold as the candidate text. In some embodiments, the computer device may also calculate an editing distance between the target text and each text in the first database, and determine a text having an editing distance to the target text less than a preset editing distance threshold as the candidate text. The preset editing distance threshold may be determined by the computer device according to an error correction accuracy.

According to the above method of determining the candidate text, the candidate text corresponding to the text of the type of wrong word may be determined by comparing the spell of the error text, or the similarity between the error text and each text in the first database, which is simple and practical, and may improve the error correction efficiency based on the candidate text.

In some embodiments, when the type of error text includes the type of absence, as shown in FIG. 15, the above-described operation 1310 "determining at least one candidate text corresponding to the error text based on the target error correction strategy and the location of the error text" may include the following operations.

In 1510, the data processing system 110 may extract a text adjacent to a text of the type of the absence from the text to be processed based on a location of the text of the type of the absence.

When the type of error text detected by the computer device is the type of the absence, the text adjacent to the text of the type of the absence may be determined and extracted from the text to be processed according to the location of the text of the type of the absence the text adjacent, so that the adjacent text may be used for later retrieval.

In 1520, the data processing system 110 may select, from a second database, a text that matches the adjacent text as the candidate text.

In some embodiments, the second database may include a medical database, such as a database of medical knowledge. The second database may be the same or different from the first database.

Specifically, when the text adjacent to the text of the type of absence is obtained, the computer device may determine the adjacent text as a target text, and retrieve a text that matches the target text from the second database according to the pronunciation, spell, text, semantic, context, etc. The retrieved text may be determined as the candidate text. For example, if the text to be processed is "hospital radiolo workflow," and the detected text of the type of the absence may be "radiolo," the text adjacent to the text of the type of the absence may be "hospital xx workflow." The computer device may determine the "hospital xx workflow" as a target text and retrieve from the second database using the target text to obtain the "hospital radiology workflow." A text that matches the text of the type of the absence may be "radiology." According to the above method of determining the candidate text, a candidate text corresponding to the text of the type of the absence may be determined by comparing the matching degree between the error text and each text in the second database, which is simple and practical, and may improve the error correction efficiency based on the candidate text.

In some embodiments, when the type of error text includes a type of disorder, as shown in FIG. 16, the above operation 1310 "determining at least one candidate text corresponding to the error text based on the target error correction strategy and the location of the error text" may include the following operations.

In 1610, the data processing system 110 may extract a text of the type of disorder from the text to be processed based on a location of the text of the type of disorder.

In some embodiments, when the type of error text detected by the computer device is the type of disorder, the text of the type of disorder may be determined and extracted from the text to be processed based on the location of the text of the type of disorder, so that the text of the type of disorder may be used for later retrieval.

In 1620, the data processing system 110 may select, from a preset third database, a text that includes the same word as the text of the type of disorder as the candidate text.

In some embodiments, the third database may include a medical database, such as a database of medical knowledge. The third database may be the same as or different from the second database.

Specifically, when the text of the type of disorder is obtained, the computer device may determine the text of the type of disorder as a target text, and retrieve a text that includes the same word as the text of the type of disorder from the third database. The retrieved text may be determined as the candidate text. For example, if the text to be processed is "radiology hospital workflow," and the detected text of the type of disorder is "radiology hospital," the text that includes the same word as the text of the type of disorder may be "hospital radiology." According to the above method of determining the candidate text, a candidate text corresponding to the text of the type of disorder may be determined by retrieving the text that includes the same word as the error text from the third database, which is simple and practical, and may improve the error correction efficiency based on the candidate text.

According to the methods of determining the candidate text described in FIG. 12 A to FIG. 16, the present disclosure may provide an implementation of the operation 1230. As shown in FIG. 17, the implementation of the operation 1230 may include the following operations.

In 1710, the data processing system 110 may add the at least one candidate text to the corresponding location in the text to be processed, and determine a score of the added text to be processed that indicating a fluency degree of the added text to be processed.

When the at least one candidate texts is obtained based on the method described in the FIG. 14 to FIG. 16, the computer device may add the at least one candidate text to the corresponding location in the text to be processed to obtain at least one added text to be processed. The computer device may input the at least one added text to be processed to into a trained language model to determine a score of the text to be processed that indicating a fluency degree of the text to be processed. The added text to be processed may be determined as smooth if the score of the fluency degree of the added text to be processed is high, and the added text to be processed may be determined as not smooth if the score of the fluency degree of the added text to be processed is low.

It should be noted that the language model may be used to analyze the smoothness degree of the added text to be processed, and grade the added text to be processed according to the smoothness degree of the added text to be processed. In practical applications, in the training of the language model, training sample data may be obtained from a medical database. The training sample data may be input to a pre-training language model for training to obtain the trained language model. The pre-training language model may be the existing BERT pre-training language model, or other pre-training language models.

In 1720, the data processing system 110 may rank the at least one text to be processed in a descending order based on the score of the at least one text to be processed, and determine the text to be processed that has a highest score as a corrected text.

After a plurality of the added text to be processed are graded, the computer device may rank the plurality of the added text to be processed in a descending order based on the scores of the plurality of the added text to be processed, and determine the text to be processed that has a highest score as a corrected text. In some embodiments, the computer device may also select, from the plurality of the added text to be processed, at least one text to be processed whose score is greater than a preset score threshold. If the count of the at least one text to be processed whose score is greater than the preset score threshold is greater than one, the computer device may select one text to be processed from the at least one text to be processed whose score is greater than the preset score threshold, or select one text to be processed according to a preset rule, and determine the selected text to be processed as the corrected text.

The method described in this embodiment may grade the smoothness degree (or fluency degree) of the added text to be processed using the trained language model. Compared with the method that only grades the error text, which has a low accuracy, the method described in this embodiment may grade the added text to be processed based on the context information of the error text, thereby improving the accuracy of error correction based on the score.

In some embodiments, when the type of error text includes a type of redundancy, an implementation of the operation 1230 may be provided. As shown in FIG. 18, the operation 1230 "performing an error correction on the error text based on the target error correction strategy and the location of the error text" may include the following operations.

In 1810, the data processing system 110 may determine, based on the target correction strategy and the location of the error text, whether to delete a text of the type of redundancy. In response to a determination of deleting the text of the type of redundancy, operation 1820 may be performed. In response to a determination of not deleting the text of the type of redundancy, operation 1830 may be performed.

Specifically, when the type of error text includes the type of redundancy, the computer device may input the text of the type of redundancy into a trained language model to detect whether the redundancy type text is smooth. In some embodiments, the computer device may extract a text including the text of the redundancy type from the text to be processed, and input the extracted text into the trained language model to detect whether the extracted text is smooth. If the extracted text is smooth, it indicates that the text of the redundancy type is not a redundant text in the text to be processed. If the extracted text is not smooth, it indicates that the text of the redundancy type is a redundant text in the text to be processed. In some embodiments, the trained language model may output a result of "smooth" or "not smooth." For example, the trained language model may output "1" that represents "smooth," or "0" that represents "not smooth." In some embodiments, the trained language model may output a value indicating the smoothness degree. For example, the trained language model may output "90%" that indicates the smoothness degree is 90%. A text whose smoothness degree is greater than or equal to a certain threshold (e.g., 30%, 40%, 50%, 60%, 70%, 80%, 90%, 95%, etc.) may be considered smooth, and a text whose smoothness degree is less than the certain threshold may be considered not smooth.

It should be noted that the language model is used to analyze the text of the type of redundancy or the text containing the text of the type of redundancy, and outputs an analysis result containing a result of smooth or not smooth. In practical applications, in the training of the language model, training sample data may be obtained from the medical database, and the training sample data may be input to the preset pre-training language model for training to obtain the trained language model. The pre-training language model may be the existing BERT pre-training language model, or other pre-training language models.

In 1820, the data processing system 110 may delete the error text in the text to be processed.

This embodiment relates to an application scenario in which the computer device determines that the text of the type of redundancy is required to be deleted. In this scenario, the computer device may directly perform the deletion operation of the text of the type of redundancy in the text to be processed.

In 1830, the data processing system 110 may not perform a deletion operation.

This embodiment relates to an application scenario in which the computer device determines that the text of the type of redundancy is not required to be deleted. In this scenario, the computer device may not perform the deletion operation.

Figure 19:
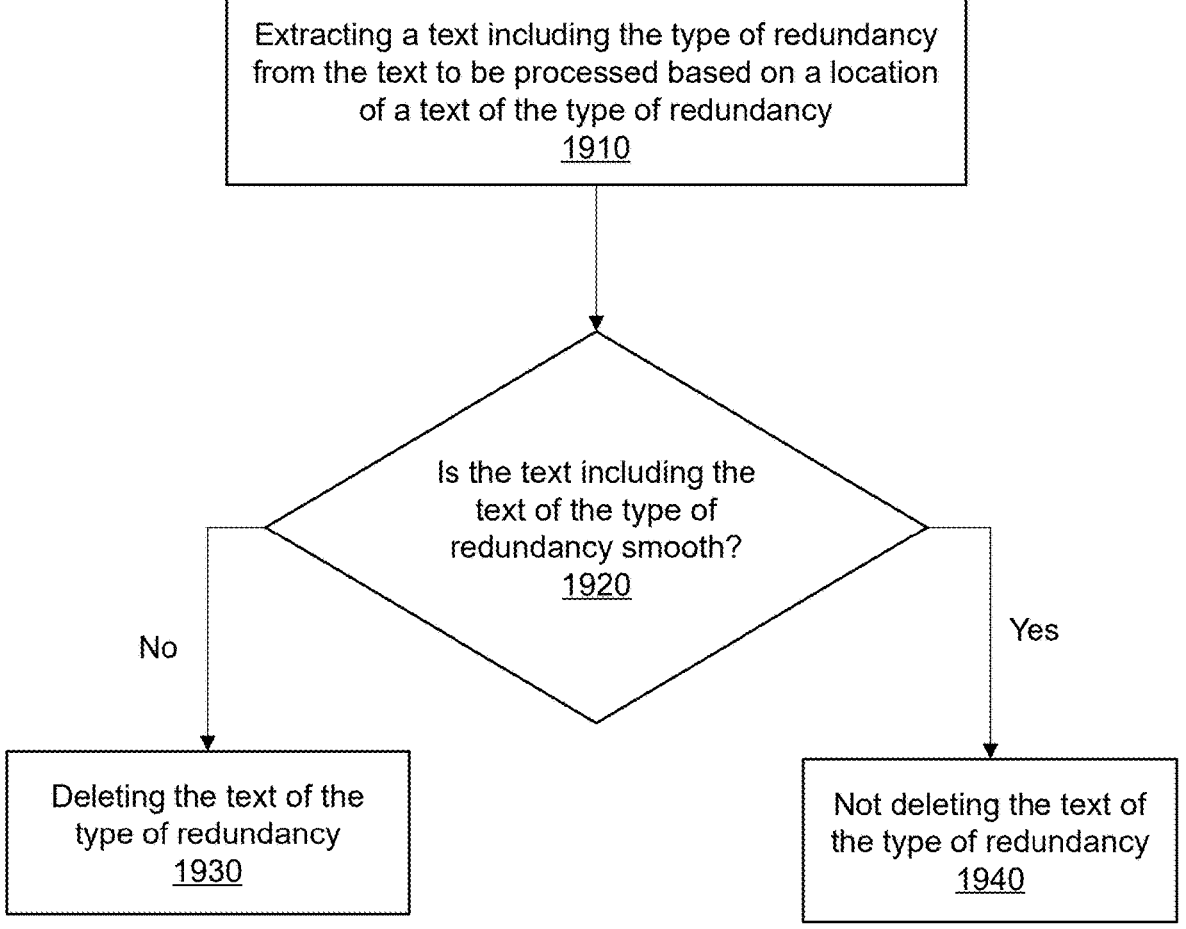
FIG. 19 is a flowchart illustrating an exemplary process for an error correction of a text of a type of redundancy according to some embodiments of the present disclosure.
Figure 20:
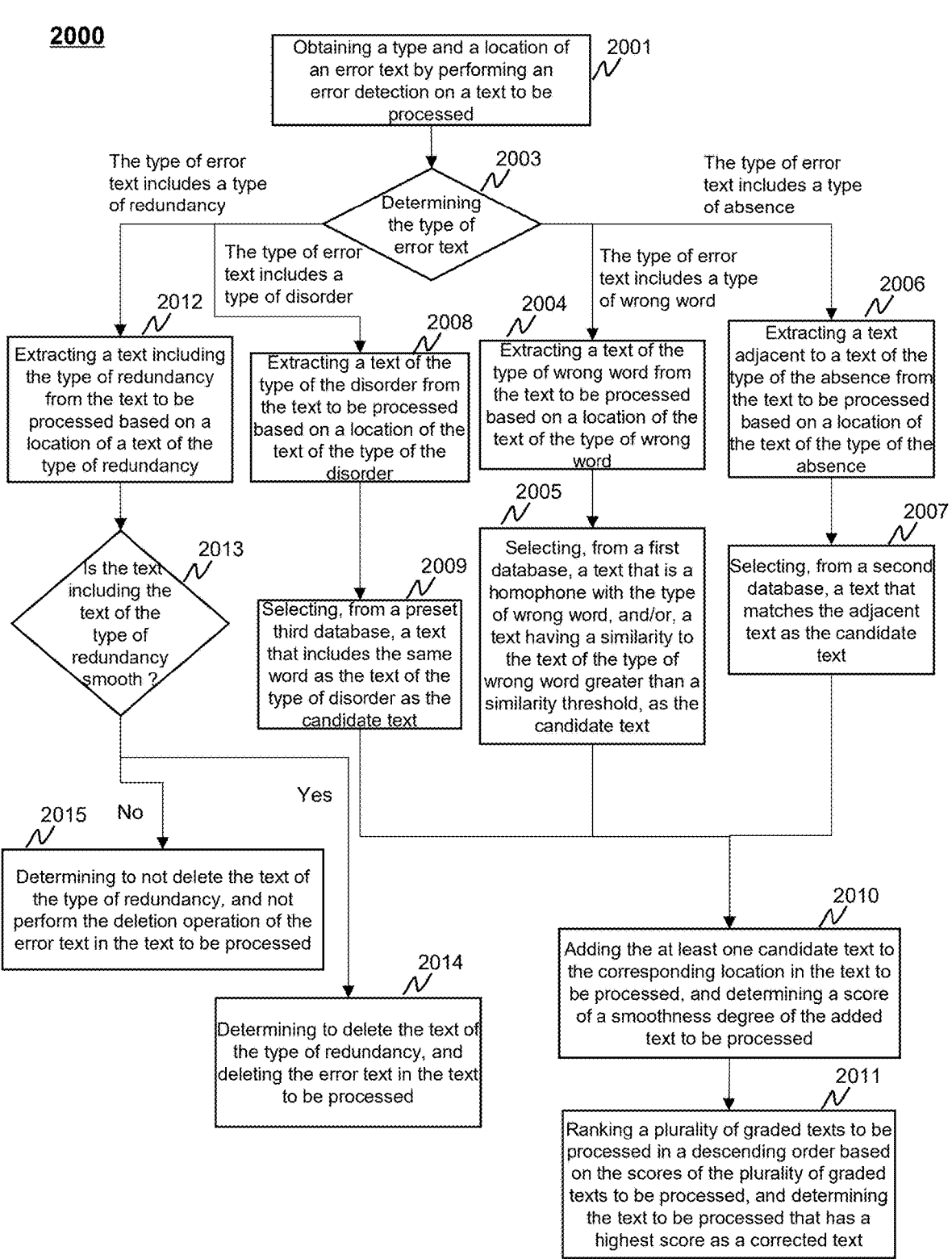
FIG. 20 is a flowchart illustrating an exemplary process for data processing according to some embodiments of the present disclosure.

In some embodiments, as shown in FIG. 19, the operation 1810 "determining, based on the target correction strategy and the location of the error text, whether to delete a text of the type of redundancy" may include the following operations.

In 1910, the data processing system 110 may extract a text including the type of redundancy from the text to be processed based on a location of a text of the type of redundancy.

In some embodiments, when the type of error text is the type of redundancy, the computer device may determine and extract the text of the type of redundancy from the text to be processed based on the location of the text of the type of redundancy, so that the text containing the text of the type of redundancy may be used for later retrieval. For example, if the text to be processed is "hospital radiology radiology workflow," the text of the type of redundancy is "radiology radiology." The extracted text including the text of the type of redundancy may be "radiology radiology workflow" or "hospital radiology radiology." The length of text including the text of the type of redundancy may be determined by the computer device, which is not limited here.

In 1920, the data processing system 110 may determine whether the text including the text of the type of redundancy is smooth. In response to determining that the text including the text of the type of redundancy is not smooth, the operation 1930 may be performed. In response to determining that the text including the text of the type of redundancy is smooth, the operation 1940 may be performed.

In 1930, the data processing system 110 may delete the text of the type of redundancy.

In 1940, the data processing system 110 may not delete the text of the type of redundancy.

In some embodiments, when the text including the text of the type of redundancy is obtained, the computer device may input the obtained text into a trained language model to determine whether the obtained text is smooth. In response to determining that the obtained text is not smooth, the computer device may determine to delete the text of the type of redundancy. In response to determining that the obtained text is smooth, the computer device may not delete the text of the type of redundancy.

The method described in this embodiment may analyzes the text including the text of the type of redundancy using the trained language model to determine whether the text is smooth. Compared with the method that only analyzes the text of the type of redundancy, which has a low accuracy, the method described in this embodiment may determine, based on the context information of the text of the type of redundancy, whether the text of the type of redundancy needs to be deleted, thereby improving the accuracy of error correction of the text of the type of redundancy.

The present disclosure may provide a data processing method according to all of the above embodiments. As shown in the FIG. 20, the data processing method may include the following operation.

In 2001, the data processing system 110 may obtain a type and a location of an error text by performing an error detection on a text to be processed.

In 2003, the data processing system 110 may determine the type of error text. When the type of error text includes a type of wrong word, operations 2004, 2005, 2010, and 2011 may be performed. When the type of error text includes a type of absence, operations 2006, 2007, 2010, and 2011 may be performed. When the type of error text includes a type of disorder, operations 2008, 2009, 2010, and 2011 may be performed. When the type of error text includes a type of redundancy, operations 2012-2015 may be performed.

In 2004, the data processing system 110 may extract a text of the type of wrong word from the text to be processed based on a location of the text of the type of wrong word.

In 2005, the data processing system 110 may select, from a first database, a text that is a homophone with the type of wrong word, and/or, a text having a similarity to the text of the type of wrong word greater than a similarity threshold, as the candidate text.

In 2006, the data processing system 110 may extract a text adjacent to a text of the type of the absence from the text to be processed based on a location of the text of the type of the absence.

In 2007, the data processing system 110 may select, from a second database, a text that matches the adjacent text as the candidate text.

In 2008, the data processing system 110 may extract a text of the type of disorder from the text to be processed based on a location of the text of the type of disorder.

In 2009, the data processing system 110 may select, from a preset third database, a text that includes the same word as the text of the type of disorder as the candidate text.

In 2010, the data processing system 110 may add the at least one candidate text to the corresponding location in the text to be processed, and determine a score of a smoothness degree of the added text to be processed.

In 2011, the data processing system 110 may rank a plurality of graded texts to be processed in a descending order based on the scores of the plurality of graded texts to be processed, and determine the text to be processed that has a highest score as a corrected text.

In 2012, the data processing system 110 may extract a text including the type of redundancy from the text to be processed based on a location of a text of the type of redundancy.

In 2013, the data processing system 110 may determine whether the text including the text of the type of redundancy is smooth. In response to determining that the text including the text of the type of redundancy is not smooth, the operation 2014 may be performed. In response to determining that the text including the text of the type of redundancy is smooth, the operation 2015 may be performed.

In 2014, the data processing system 110 may determine to delete the text of the type of redundancy, and delete the error text in the text to be processed.

In 2015, the data processing system 110 may determine to not delete the text of the type of redundancy, and not perform the deletion operation of the error text in the text to be processed.

In some embodiments, in response to determining that a location of the text to be processed includes a plurality of types of errors, the above processing strategies may be sequentially performed according to a preset order.

The above operations may be found elsewhere in this disclosure, and the descriptions of which are not repeated here.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the above operations may be performed by the user terminal 130, such as the CPU 340, the GPU 330, and/or one or more modules described in the FIG. 22.

Figure 21:
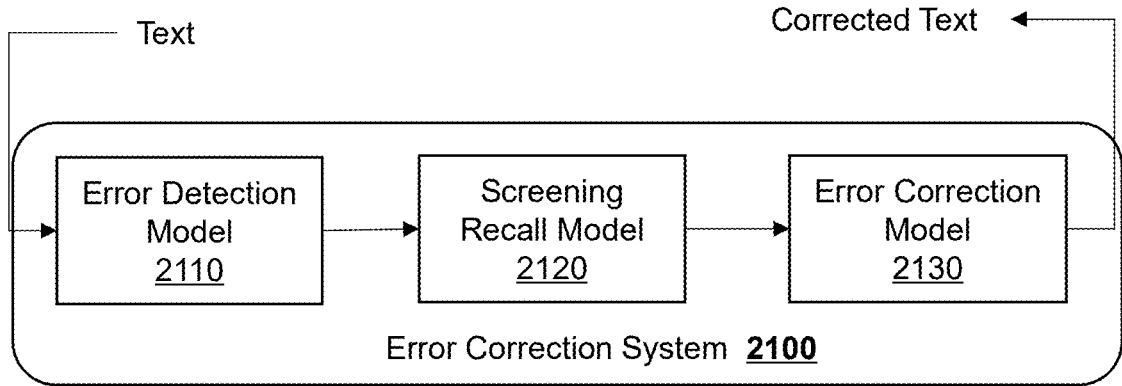
FIG. 21 is a schematic diagram illustrating an exemplary error correction system according to some embodiments of the present disclosure.

According to all of the above embodiments, the present disclosure also provides an error correction system 2100. As shown in FIG. 21, the error correction system 2100 may include an error detection model 2110, a screening recall model 2120, and an error correction model 2130. An output end of the error detection model 2110 may be connected to an input end of the screening recall model 2120, and an output of the screening recall model 2120 may be connected to an input end of the error correction model 2130. In some embodiments, the error detection model 2110 may be used to detect an error text in the input text, and output a type and a location of the error text. When the error text includes at least one of a type of wrong word, a type of absence, and a type of disorder, the screening recall model 2120 may be used to select an error correction strategy corresponding to the type of the error text according to the type of error text output by the error detection model, and then determine at least one candidate text corresponding to the error text based on the selected error correction strategy and the location of the error text in a preset database. The error correction model 2130 may determine a score of a smoothness degree of the at least one candidate text, and perform an error correction processing for the text to be processed according to a candidate text that has a highest score. When the type of the error text includes a type of redundancy, the screening recall model 2120 may be used to detect whether the text of the type of redundancy or a text including the text of the type of redundancy is smooth to determine whether the text of the type of redundancy needs to be deleted. If the screening recall model 2120 determines that the text of the type of redundancy (or the text including the text of the type of redundancy) is smooth, the error correction model 2130 may do not perform the deletion operation. If the screening recall model 2120 determines that the text of the type of redundancy (or the text including the text of the type of redundancy) is not smooth, the error correction model 2130 may delete the text of the type of redundancy in the text to be processed. The data processing method may be applied to the error correction system to perform the error correction processing for a text. Regarding the functions and implementation methods of models or components of the error correction system may be found in the above embodiments, and the descriptions of which are not repeated here. In some embodiments, hardware and/or software of the data processing system 110 and/or the user terminal 130 may be implemented based on the error correction system 2100.

In some embodiments, the type of error text may also include a content error. For example, an image report may include target images and texts. If the content of a text does not correspond to other texts or target images, the text may be an error text, and the type of error text may be a content error. For example, as shown in FIG. 10, if an examination item in the imaging report is "axial CT scan of the head," and the image description and diagnosis of the image report is related to a description of the chest, the image description and diagnosis in the image report may be an error text, and the type of error text may be a content error. As another example, if a target image in the image report is a head image, and the image description and diagnosis in the image report is related to a description of the chest, the image description and diagnosis in the image report may be an error text, and the type of error text may be a content error.

As an example, the image report may be input into a trained word segmentation model, and the trained word segmentation model may output a plurality of words of the text in the image report. The plurality of words may be input into a trained word recognition model to determine unrelated words in the plurality of words. The text where the unrelated words recognized by trained word recognition model are located may be determined as the error text and the type and location of the error text may be determined. As still another example, the target image in the image report may be extracted, and the extracted target image may be input into an image recognition model to obtain the image features output by the image recognition model. The image features and the plurality of words described above may be into the trained word recognition model to determine the words that are not related to the image features in the plurality of words. The text where the unrelated words recognized by trained word recognition model are located may be determined as the error text and the type and location of the error text may be determined. In some embodiments, after the text with content error is recognized, a text for replacing the error text may be retrieved from the knowledge graph using the method described in FIG. 4-FIG. 11 to update the image report.

Figure 22:
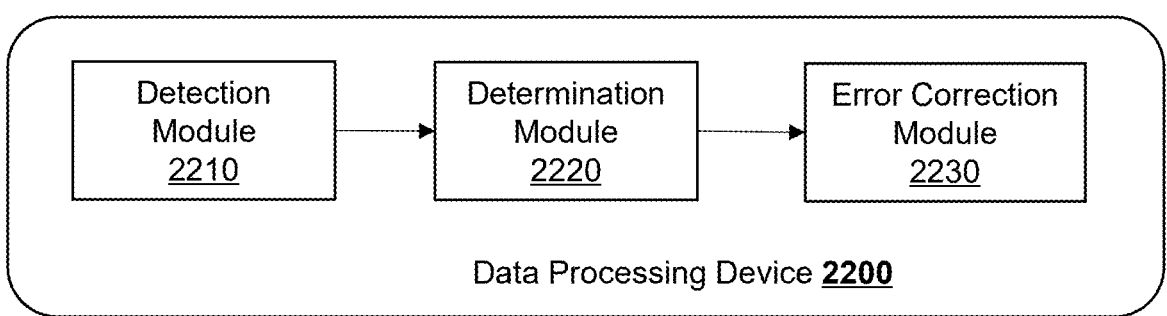
FIG. 22 is a schematic diagram illustrating an exemplary data processing device according to some embodiments of the present disclosure.

In some embodiments, as shown in FIG. 22, a data processing device 2200 may be provided, and the data processing device 220 may include:

a detection module 2210 configured to obtain a type and a location of an error text by performing an error detection on a text to be processed;

a determination module 2220 configured to determine a target error correction strategy corresponding to the type of the error text based on a corresponding relationship between the type of the error text and an error correction strategy;

an error correction module 2230 configured to perform an error correction on the error text based on the target error correction strategy and the location of the error text.

More descriptions for the data processing device 2200 may be found elsewhere in the present disclosure, the descriptions of which are not repeated here. Each module of the data processing device may be implemented in all or portions through software, hardware, and combinations thereof. The modules may be embedded or independent of the processor in the computer device, and may be also stored in a storage device in a computer device in a software form to facilitate the processor perform the operations corresponding to each module. In some embodiments, the hardware and/or software of the data processing system 110 and/or the user terminal 130 may be implemented based on the data processing device 2200.

In some embodiments, the present disclosure provides a computer readable storage medium that stores a computer program. The computer program may be executed by a processor (e.g., the data processing system 110, the user terminal 130, the processor 210, the CPU 340, the GPU 330, the error correction system 2100, or one or more modules described in FIG. 22) to implement at least one of the process 1200-the process 2000.

With the continuous development and innovation of medical informatization, a large amount of medical data is generated, and most of these medical data is unstructured data. With the development of medical equipment technology and the progress of examination methods, a large amount of unstructured data may also be generated with the improvement of medical standards. Therefore, the storage of these unstructured medical data becomes particularly important. In a conventional technique, unstructured medical data is stored using customized interfaces, backup software and tape libraries or virtual tape libraries based on data identifier of unstructured medical data. However, when unstructured medical data is stored using the conventional technique, it takes a long time to scan the file system only once, which has a low storage efficiency. The present disclosure provides an unstructured data storage method, system, processing device, and storage medium with an improving storage efficiency.

FIG. 23 is a flowchart illustrating an exemplary unstructured data storage process 2300 according to some embodiments of the present disclosure. In some embodiments, the process 2300 may be implemented in the medical system 100 (e.g., the data processing system 110). For example, the process 2300 may be executed by a server of a medical system. Exemplary medical systems may include a picture archiving and communication systems (PACS), a post-processing workstation, a surgical system, a hospital information system (HIS), a laboratory information management system (LIS), a radiology information system (RIS), a doctor workstation, a nurse workstation, an imaging system, a hospitalization management system, a door agency management system, or a charging system. For example, the process 2300 may be executed by the processor 210. As another example, the process 2300 can be executed by one or more modules illustrated in FIG. 27. In some embodiments, the process 2300 may be stored in a storage medium (e.g., the storage device 140) as a form of instructions or programs, and the process 2300 may be implemented when the instructions or programs are executed by the medical system 100. The operations of the illustrated process 2300 presented below are intended to be illustrative. In some embodiments, the process 2300 may be accomplished with one or more additional operations not described, and/or without one or more of the operations discussed. Additionally, the order in which the operations of the process 2300 as illustrated in FIG. 23 and described below is not intended to be limiting.

In 2310, the data processing system 110 may obtain an unstructured medical data to be stored.

In some embodiments, unstructured data refers to data that cannot be represented in database tables using two-dimensional logic. Unstructured medical data may refer to data related to the medical system 100 such as office documents, texts, pictures, Extensive Markup Language (XML), Hypertext Markup Language (HTML), various reports, audios, and videos, etc. For example, the unstructured medical data may include unstructured medical image data (e.g., a computed tomography (CT) image, a magnetic resonance imaging (MRI) image, a PET image, a molecular imaging (MI) image, an X-rays (XR) image, an ultrasound image, etc.), an image report, a diagnostic report, a laboratory test form, an application form, and texts, pictures, audios, videos, etc. obtained by the medical system 100 from external devices.

Specifically, the computer device (e.g., the data processing system 110) may obtain the unstructured medical data to be stored. In some embodiments, the computer device may obtain unstructured medical data to be stored from components of the medical system 100. For example, the computer device may obtain unstructured medical data to be stored from a server of a PACS. As another example, the computer device may obtain unstructured medical data to be stored in real time from a medical imaging device. In some embodiments, the computer device may obtain the unstructured medical data to be stored from an external device of the medical system 100. In some embodiments, after the unstructured medical data to be stored is obtained, the computer device may first preprocess the unstructured medical data to be stored and remove the redundant data in the unstructured medical data to be stored.

In 2320, the data processing system 110 may obtain structured medical data corresponding to the unstructured medical data and a corresponding relationship (index information) between the unstructured medical data and the structured medical data by analyzing the unstructured medical data.

Structured data refers to data that is logically expressed and implemented by the two-dimensional table structure. The unstructured data may be parsed by offline analyzing or online analyzing. Specifically, the computer device may analyze the unstructured medical data to be stored to obtain the structured medical data corresponding to the unstructured medical data and the corresponding relationship between the unstructured medical data and the resulting structured medical data. In some embodiments, the computer device may analyze the unstructured medical data to be stored using a preset image analyzing method or a text extraction method to obtain a structural medical data corresponding to the unstructured medical data to be stored. The computer device may further obtain the corresponding relationship between the unstructured medical data and the structured medical data according to the unstructured medical data to be stored and the obtained structured medical data. In some embodiments, the computer device may obtain the corresponding relationship between the unstructured medical data to be stored and the structured medical data according to the analyzing path for analyzing unstructured medical data to be stored. It should be noted that analyzing methods corresponding to different types of unstructured data are different. Accordingly, the corresponding relationships between the unstructured medical data and the structured medical data corresponding to different types of unstructured data are also different. In some embodiments, the computer device may determine an analyzing method corresponding to the unstructured medical data to be stored according to the type of unstructured medical data to be stored, and analyze the unstructured medical data to obtain the structural medical data corresponding to the unstructured medical data. In some embodiments, the computer device may perform a largest set of standard processing for corresponding relationships between the unstructured medical data and the structured medical data corresponding to different types of unstructured data as needed, that is, the computer device may perform the largest set of standard processing for corresponding relationships between the unstructured medical data and the structured medical data according to needs of users, and store corresponding relationships between the unstructured medical data and the structured medical data to different sets.

In 2330, the data processing system 110 may store the structured medical data and the corresponding relationship into a preset fourth database, and store the unstructured medical data into a preset fifth database.

Specifically, the computer device may store the corresponding relationship between the structured medical data and the unstructured medical data and the structured medical data to the preset fourth database, and store the unstructured data to be stored to the preset fifth database. In some embodiments, the preset fourth database may be a DB database, and the preset fifth database may be an object storage database. In some embodiments, the computer device may store the structured medical data and the obtained corresponding relationship between the unstructured medical data and the structured medical data to the preset fourth database in real time or according to a preset time interval, such as, 5 seconds, etc. Accordingly, the computer device may store the unstructured medical data to be stored to the preset fifth database in real time or according to the preset time interval.

According to the unstructured data storage method, since the process of analyzing the unstructured medical data is very simple, the computer device may quickly and accurately obtain structured medical data corresponding to the unstructured medical data to be stored and the corresponding relationship between the unstructured medical data and the obtained structured medical data, so that the computer device may quickly store the obtained structured medical data and the corresponding relationship to the preset fourth database, and store the unstructured medical data to be stored to the preset fifth database, thereby improving the storage efficiency of unstructured medical data to be stored.

In the above scenario in which the unstructured medical data to be stored is analyzed to obtain the structured medical data corresponding to the unstructured medical data to be stored and the corresponding relationship between the unstructured medical data and the structured medical data, in some embodiments, as shown in FIG. 24, the operation 2320 may include the following operations.

In 2410, the data processing system 110 may obtain the structured medical data corresponding to the unstructured medical data by analyzing the unstructured medical data using a preset analysis rule.

Specifically, the computer device may obtain the structured medical data corresponding to the unstructured medical data to be stored by analyzing the unstructured medical data to be stored using the preset analysis rule. In some embodiments, the preset analysis rule may be a preset text analysis rule, a preset image analysis rule, or a preset report analysis rule. For instance, the computer device may analysis the text of the unstructured data to be stored to obtain the structured medical data corresponding to the unstructured data to be stored using a preset text analysis rule.

In 2420, the data processing system 110 may construct a corresponding relationship between the unstructured medical data and the structured medical data based on a data identifier of the unstructured medical data and a data identifier of the structured medical data.

Specifically, the computer device may construct the corresponding relationship between the unstructured medical data to be stored and the obtained structured medical data based on the data identifier of the unstructured medical data to be stored and the data identifier of the obtained structured medical data. For example, if the data identifier of the unstructured medical data to be stored is A, and the data identifier of the obtained structured medical data corresponding to the unstructured medical data to be stored is B, the constructed corresponding relationship between the unstructured medical data to be stored and the obtained structured medical data may be A-B.

In this embodiment, the process of analyzing the unstructured medical data to be stored using the preset analysis rule is very simple, so that the computer device may quickly obtain the structured medical data corresponding to the unstructured medical data to be stored, which may improve the efficiency of the obtaining of the structured medical data corresponding to the unstructured medical data to be stored. Accordingly, the computer device may quickly construct the corresponding relationship between the unstructured medical data to be stored and the obtained structured medical data based on the data identifier of the unstructured medical data to be stored and the data identifier of the obtained structured medical data, which may improve the efficiency of the obtaining of the corresponding relationship between the unstructured medical data to be stored and the obtained structured medical data.

In the above scenario in which the unstructured medical data to be stored is parsed using the preset analysis rule, the preset analysis rule may include a medical image text identification rule, a DICOM file analysis rule, and an XML report analysis rule.

Specifically, the preset analysis rule may include a medical image text identification rule, a DICOM file analysis rule, and an XML report analysis rule, that is, the computer device may obtain the structured medical data corresponding to the unstructured medical data to be stored by analyzing the unstructured medical data to be stored using the medical image text identification rule, the DICOM file analysis rule, or the XML report analysis rule. In some embodiments, the computer device may parse the unstructured medical data to be stored in real time using the medical image text identification rule, the DICOM file analysis rule, or the XML report analysis rule. Alternatively, the computer device may parse the unstructured medical data to be stored in the background using the medical image text identification rule, the DICOM file analysis rule, or the XML report analysis rule, and transmit the obtained structured medical data to the computer device. For example, each word in unstructured medical data to be stored may be identified using the medical image text identification rule by pre-configuring the meaning of each word, and parse the meaning of each word to obtain the structured medical data corresponding to the unstructured medical data to be stored. For example, the meaning of each word in an application form may be obtained by analyzing the application using the medical image text identification rule to obtain the structured medical data corresponding to the application form. The DICOM file analysis rule (also referred as to a medical digital imaging and communication rule) refers to an international standard (ISO 12052) for medical images and related information, which defines medical image formats that can be used for data exchange with quality that meets clinical needs. The unstructured medical data to be stored may be parsed using the international standard to obtain the structured medical data corresponding to the unstructured medical data to be stored. The unstructured medical data to be stored may be parsed using the XML report analysis rule by configuring a custom analysis rule. For example, a clinical document architecture (CDA) may be analyzed. In some embodiments, the CDA may provide a general document architecture, and all CDA documents may be represented by XML code. The CDA document may be parsed using the XML report analysis rule to obtain the structured medical data corresponding to the CDA document.

In this embodiment, the preset analysis rule may include the medical image text identification rule, the DICOM file analysis rule, and the XML report analysis rule. The medical image text identification rule, the DICOM file analysis rule, and the XML report analysis rule may cover a wide range, so that the computer device may fully parse the unstructured medical data to be stored, which may expand the application scenario of the preset analysis rule.

In the above scenario of the obtaining of the unstructured medical data to be stored, the computer device may obtain the unstructured medical data to be stored by a passively receiving manner or an active acquisition manner. The specific implementation of the two manners are described in detail below:

If the computer device obtains the unstructured medical data to be stored by a passively receiving manner, the operation 2310 may include receiving the unstructured medical data to be stored sent by a corresponding medical device via a preset application interface.

Specifically, the computer device may receive the unstructured medical data to be stored sent by a corresponding medical device via a preset application interface. For example, if the unstructured medical data to be stored is CT data, the computer device may receive the unstructured medical data to be stored sent by a CT device via an application interface.

In this embodiment, the computer device may completely receive the unstructured medical data to be stored sent by a medical device via the preset application interface, which may ensure the integrity of unstructured medical data to be stored received by the computer device.

If the computer device may obtain the unstructured medical data to be stored by an active acquisition manner, the operation 2310 may include obtaining the unstructured medical data to be stored by looking in a medical device corresponding to a target address identifier based on the target address identifier.

Specifically, the computer device may obtain the unstructured medical data to be stored by looking in the medical device corresponding to the target address identifier based on the target address identifier. For example, if the target address identifier is a target address identifier of an MR device, when the computer device obtains the unstructured medical data to be stored, the computer device may obtain the unstructured medical data to be stored by looking in the MR medical device corresponding to the target address identifier of the MR medical device based on the target address identifier of the MR medical device.

In this embodiment, the computer device may quickly obtain the unstructured medical data to be stored by quickly looking in the medical device corresponding to the target address identification based on the target address identification, which may improve the accuracy of the obtaining of the unstructured medical data.

In some scenarios, after the unstructured medical data to be stored and the structured medical data corresponding to the unstructured medical data to be stored is stored, the stored unstructured medical data and the structured medical data may be searched. In some embodiments, as shown in FIG. 25, the above method also includes the following operations.

In 2510, the data processing system 110 may receive a query request. The query request may include a data identifier of data to be searched.

Specifically, the computer device may receive the query request. The query request may include the data identifier of data to be searched. In some embodiments, the data identifier of data to be searched may be a data identifier of unstructured medical data, or a data identifier of structured medical data. In some embodiments, the query request received by the computer device may be one or more query requests.

In 2520, the data processing system 110 may obtain the structured medical data and the unstructured medical data corresponding to the data identifier, by looking in the fourth database and the fifth database, respectively, according to the data identifier, the corresponding relationship, and the query request.

Specifically, the computer device may obtain the structured medical data and the unstructured medical data corresponding to the data identifier of the data to be searched included in the query request, by looking in the fourth database and the fifth database, respectively, according to the data identifier of the data to be searched included in the query request and the corresponding relationship between the unstructured medical data to be stored and the structured medical data based on the received query request. In some embodiments, the computer device may obtain the structured medical data corresponding to the data identifier of the data to be searched included in the query request, by looking in the fourth database, according to the data identifier of the data to be searched included in the query request and the received query request. The computer device may obtain the unstructured medical data corresponding to the data identifier of the data to be searched included in the query request, by looking in the fifth database, according to the structured medical data corresponding to the data identifier of the data to be searched included in the query request and the corresponding relationship between the unstructured medical data to be stored and the corresponding structured medical data.

In this embodiment, the computer device may accurately obtain the structured medical data and the unstructured medical data corresponding to the data identifier of the data to be searched included in the query request, by looking in the fourth database and the fifth database, respectively, according to the data identifier of the data to be searched included in the query request and the corresponding relationship between the unstructured medical data to be stored and the corresponding structured medical data based on the received query request, thereby improving the accuracy and efficiency of the obtaining of the structured medical data and the unstructured medical data corresponding to the query request.

Figure 26A:
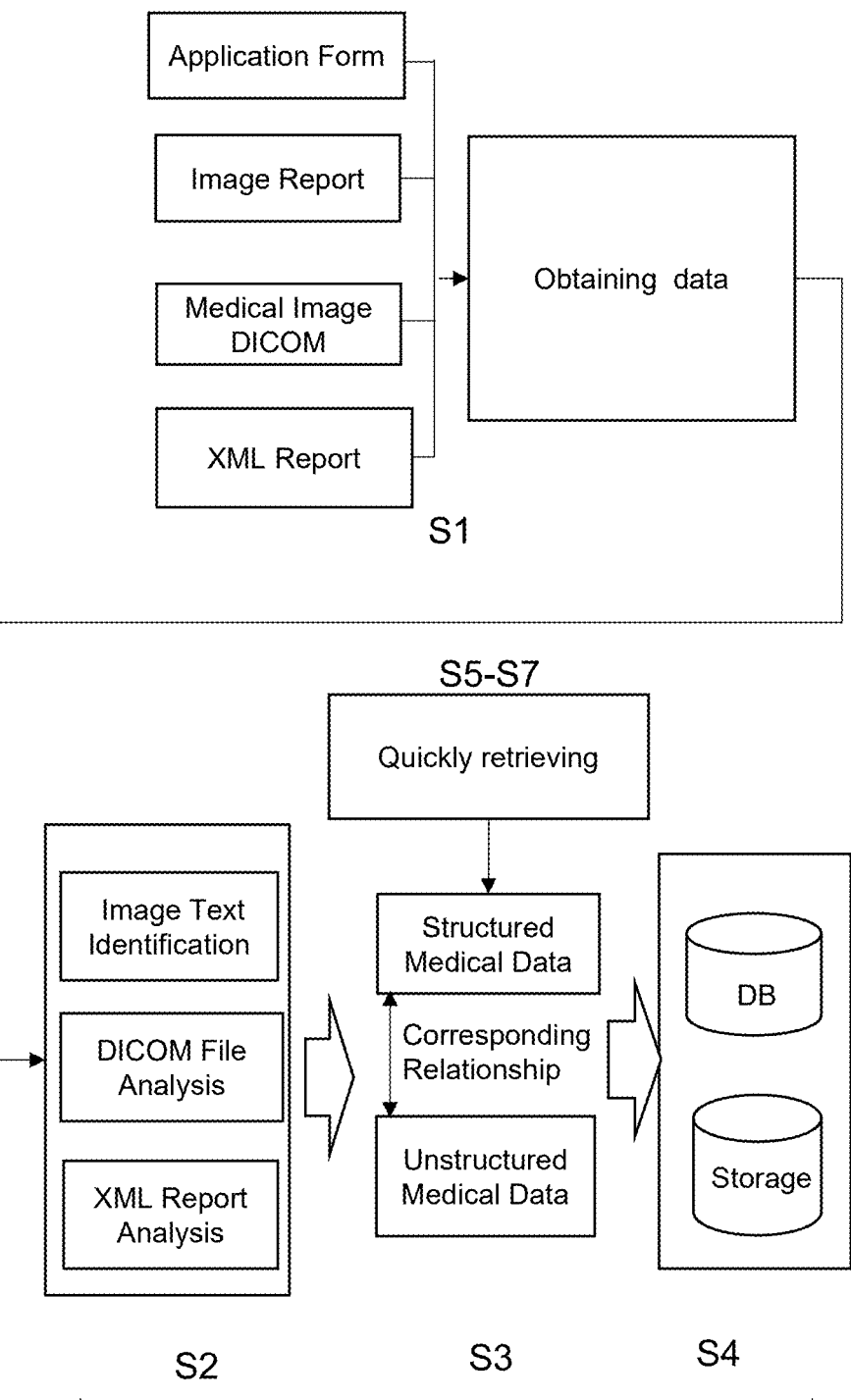
FIG. 26A is a flowchart illustrating an exemplary unstructured data storage process according to some embodiments of the present disclosure.
Figure 26B:
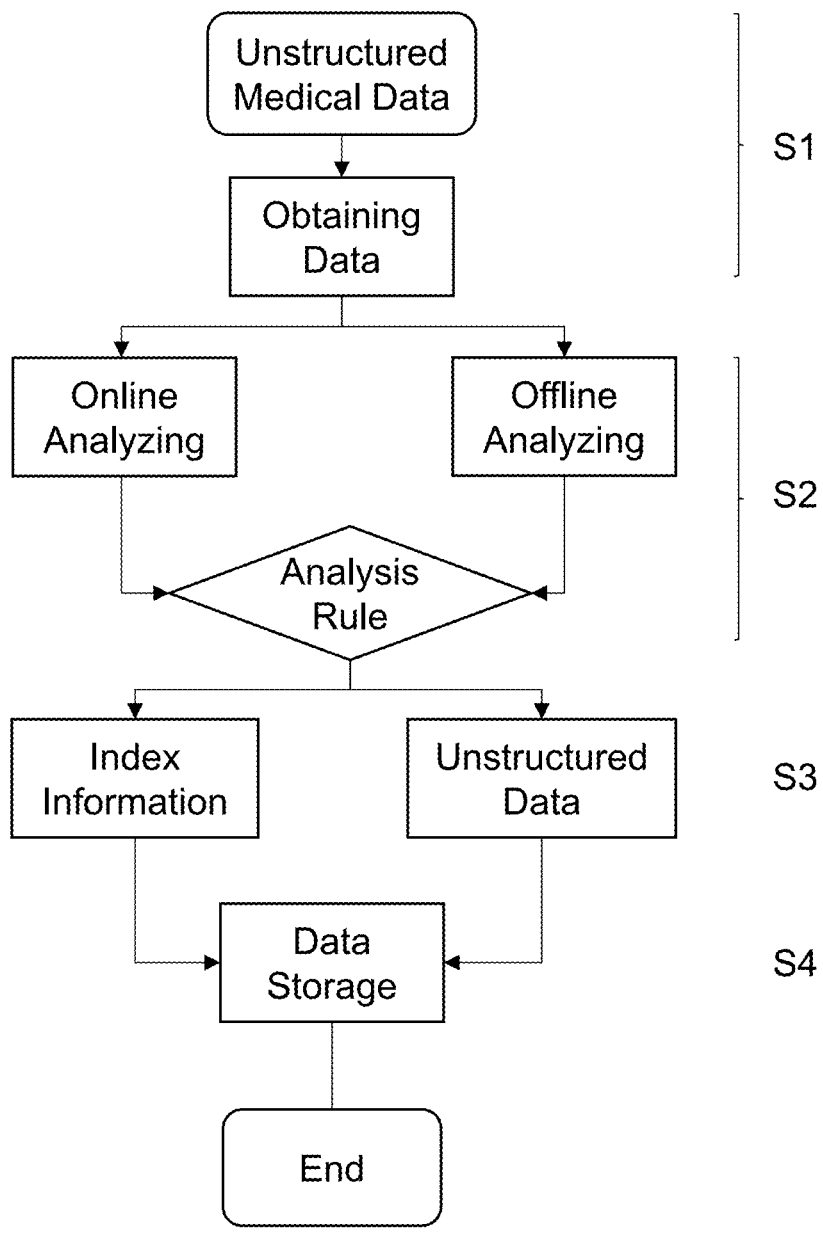
FIG. 26B is a flowchart illustrating an exemplary unstructured data storage process according to some embodiments of the present disclosure.

In order to facilitate understanding of those skilled in the art, the unstructured data storage method provided by the present disclosure is described in detail, as shown in FIG. 26A and FIG. 26 B, which may include the following operations.

In S1, the data processing system 110 may receive the unstructured medical data to be stored sent by a corresponding medical device via a preset application interface, or obtain the unstructured medical data to be stored by looking in a medical device corresponding to a target address identifier based on the target address identifier.

In S2, the data processing system 110 may obtain the structured medical data corresponding to the unstructured medical data by analyzing the unstructured medical data using a preset analysis rule. The preset analysis rule may include a medical image text identification rule, a DICOM file analysis rule, and an XML report analysis rule.

In S3, the data processing system 110 may construct a corresponding relationship between the unstructured medical data and the structured medical data based on a data identifier of the unstructured medical data and a data identifier of the structured medical data.

In S4, the data processing system 110 may store the structured medical data and the corresponding relationship into a preset fourth database, and store the unstructured medical data into a preset fifth database.

In S5, the data processing system 110 may receive a query request including a data identifier of data to be searched.

In S6, the data processing system 110 may obtain the structured medical data corresponding to the data identifier by looking in the fourth database according to the data identifier and the query request.

In S7, the data processing system 110 may obtain the unstructured medical data corresponding to the data identifier by looking in the fifth database based on the structured medical data corresponding to the data identifier and the corresponding relationship.

It should be noted that more descriptions for operations S1-S7 may be found elsewhere in the present disclosure, the descriptions of which are not repeated here.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 27:
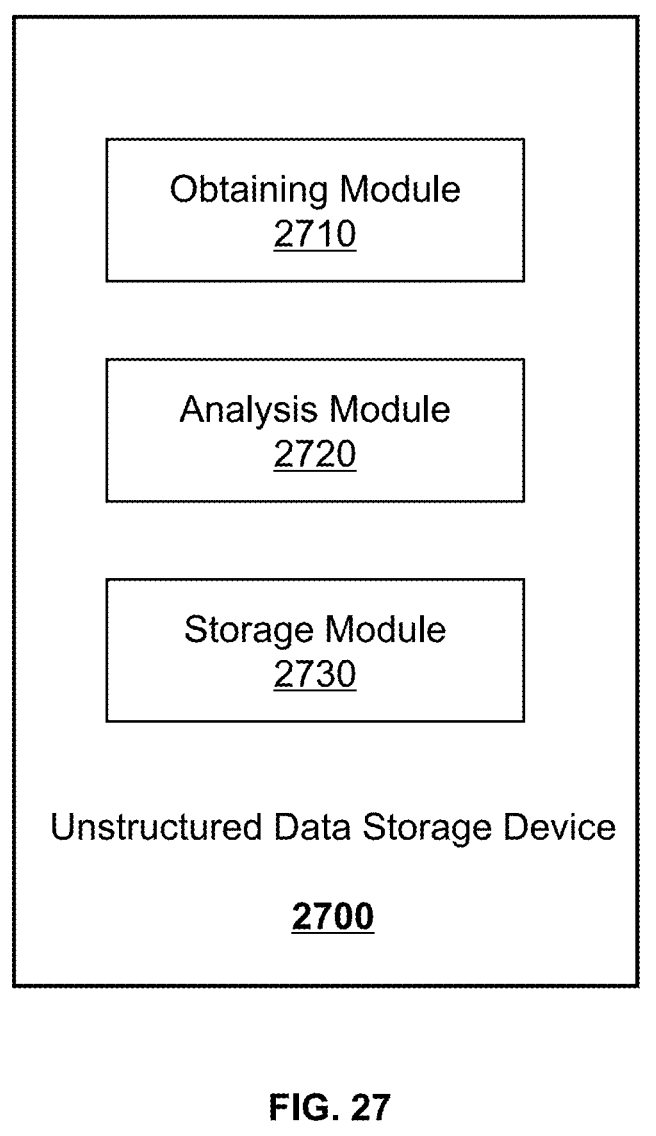

In some embodiments, as shown in FIG. 27, an unstructured data storage device 2700 is provided. The unstructured data storage device 2700 may include an obtaining module 2710, an analysis module 2720, and a storage module 2730.

The obtaining module 2710 may be configured to obtain unstructured medical data to be stored.

The analysis module 2720 may be configured to obtain structured medical data corresponding to the unstructured medical data and a corresponding relationship between the unstructured medical data and the structured medical data by analyzing the unstructured medical data.

The storage module 2730 may be configured to store the structured medical data and the corresponding relationship into a fourth database, and store the unstructured medical data into a fifth database.

The unstructured data storage device 2700 provided in this embodiment may perform the above embodiments for describing methods, and the descriptions of which are not repeated here.

In some embodiments, the analysis module 2720 may include an analysis unit and a constructing unit.

The analysis unit may be configured to obtain the structured medical data corresponding to the unstructured medical data by analyzing the unstructured medical data using a preset analysis rule.

The constructing unit may be configured to construct the corresponding relationship between the unstructured medical data and the structured medical data based on a data identifier of the unstructured medical data and a data identifier of the structured medical data.

In some embodiments, the preset analysis rule may include a medical image text identification rule, a DICOM file analysis rule, and an XML report analysis rule.

The unstructured data storage device provided in this embodiment may perform the above embodiments for describing methods, and the descriptions of which are not repeated here.

In some embodiments, the obtaining module 2710 may include a first acquisition unit.

The first acquisition unit may be configured to receive the unstructured medical data to be stored sent by a corresponding medical device via a preset application interface.

The unstructured data storage device provided in this embodiment may perform the above embodiments for describing methods, and the descriptions of which are not repeated here.

In some embodiments, the obtaining module may 2710 include a second acquisition unit.

The second acquisition unit may be configured to obtaining the unstructured medical data to be stored by looking in a medical device corresponding to a target address identifier based on the target address identifier.

The unstructured data storage device provided in this embodiment may perform the above embodiments for describing methods, and the descriptions of which are not repeated here.

In some embodiments, the unstructured data storage device may include a receiving module and a query module.

The receiving module may be configured to receive a query request. The query request may include a data identifier of data to be searched.

The query module may be configured to obtain the structured medical data and the unstructured medical data corresponding to the data identifier, by looking in the fourth database and the fifth database, respectively, according to the data identifier and the corresponding relationship based on the query request.

The unstructured data storage device provided in this embodiment may perform the above embodiments for describing methods, and the descriptions of which are not repeated here.

In some embodiments, the query module may include a first query unit and a second query unit.

The first query unit may be configured to obtain the structured medical data corresponding to the data identifier by looking in the fourth database according to the data identifier based on the query request.

The second query unit may be configured to obtain the unstructured medical data corresponding to the data identifier by looking in the fifth database based on the structured medical data corresponding to the data identifier and the corresponding relationship.

The unstructured data storage device provided in this embodiment may perform the above embodiments for describing methods, and the descriptions of which are not repeated here.

More descriptions for the unstructured data storage device may be found elsewhere in the present disclosure, the descriptions of which are not repeated here. Each module of the unstructured data storage device may be implemented in all or portions through software, hardware, and combinations thereof. The modules may be embedded or independent of the processor in the computer device, and may be also stored in a storage device in a computer device in a software form to facilitate the processor perform the operations corresponding to each module.

In some embodiments, the present disclosure provides a computer readable storage medium that stores a computer program. The computer program may be executed by a processor (e.g., the data processing system 110, the user terminal 130, the processor 210, the CPU 340, the GPU 330, the error correction system 2100, or one or more modules described in FIG. 27) to implement at least one of the processes 2300-2500, 2600A, and 2600B.

Figure 28:
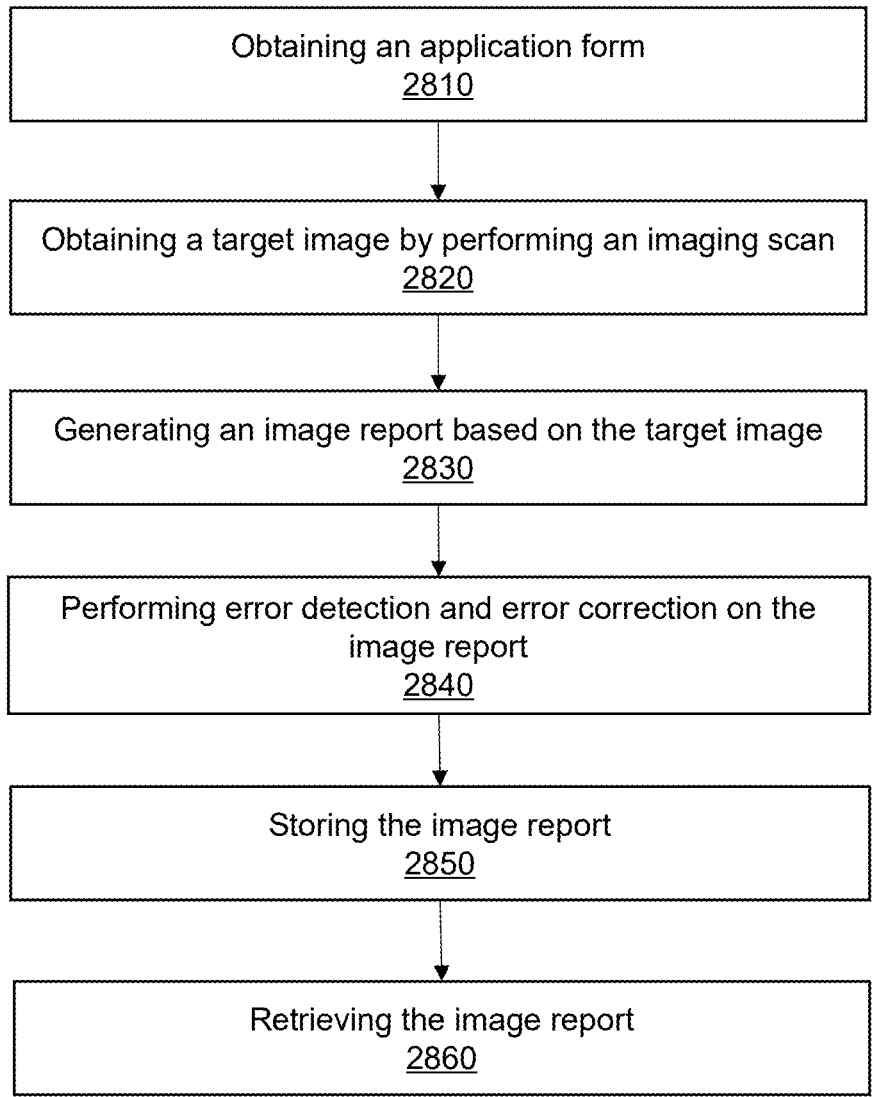
FIG. 28 is a flowchart illustrating an exemplary workflow of a medical system according to some embodiments of the present disclosure.

FIG. 28 is a flowchart illustrating an exemplary workflow of a medical system according to some embodiments of the present disclosure. The process 2800 may include a workflow for image examination using the medical system 100.

As shown in FIG. 28, the process 2800 may include the following operations.

In 2810, an application form may be obtained.

The application form may be a document with a request for photographing a medical image. In some embodiments, the format of the application form may be a document, a picture, or the like. In some embodiments, the request for photographing a medical image may be recorded on the application form in the form of text. In some embodiments, the request for photographing a medical image include information relating to the photographing of a medical image, such as patient information, photographing information, or the like. Exemplary patient information may include a name, an age, a gender, etc. Exemplary photographing information may include a region of interest (e.g., the brain, the chest, a lung, the abdomen, the heart, a skeleton, etc.), a type of image (e.g., a CT image, a MR image, a PET image, an X-ray image, an ultrasound image, etc.), an examination time, etc.

In some embodiments, the application form may be stored in such as a HIS, or a system related to image photographing (e.g., a RIS, an imaging system). The application may be unstructured data, and the application form may be stored according to the storage of the unstructured data described in FIG. 23-FIG. 28. For example, structured medical data corresponding to the application form and a corresponding relationship between the application form and the structured medical data may be obtained by analyzing the application form. The structured medical data and the corresponding relationship may be stored in the fourth database, and the application form may be stored in the fifth database.

In some embodiments, the HIS may be communicated with the RIS or an imaging system via network 120. After the HIS obtains the application form, the application form may be sent to the RIS or the imaging system, and the RIS or the imaging system may prepare or perform to photograph after receiving the application form. In some embodiments, the HIS may be not communicated with the RIS or an imaging system. The RIS or the imaging system may extract and identify the text in the paper application form to obtain relevant information in the application form. For example, the text in the application form may be extracted and identified by a preset identification algorithm. In some embodiments, the preset identification algorithm may include an optical character recognition (OCR) algorithm.

The ORC algorithm may include, but are not limited to a Connectionist Temporal Classification (CTC) algorithm, a convolutional recurrent neural network (CRNN) algorithm, a connectionist text proposal network (CPTN) algorithm, a multi-label classification algorithm, etc.

In some embodiments, an error detection and an error correction may be performed for the text in the extracted application form. For example, the text in the extracted application form may be used as a text to be processed, and the error detection may be performed for the text to be processed to obtain a type and a location of an error text. A target error correction strategy corresponding to the type of the error text may be determined based on a corresponding relationship between the type of the error text and an error correction strategy. The error correction on the error text may be performed based on the target error correction strategy and the location of the error text. More descriptions for the error detection and the error correction of the text in the extracted application form may be found elsewhere in the present disclosure (e.g., FIGS. 12-22 and the descriptions thereof).

In 2820, a target image may be obtained by performing an imaging scan. After the application form is obtained, the RIS or the imaging system may perform an imaging scan according to the application form to obtain the target image.

In 2830, an image report may be generated based on the target image.

In some embodiments, after the target image is generated, the RIS or the imaging system may generate an image report based on the target image. In some embodiments, the RIS or the imaging system may send the generated target image to a PACS and/or a post-processing workstation, and the PACS and/or a post-processing workstation may generate an image report based on the target image. In some embodiments, the image report may be automatically generated according to the image report generation method described in FIG. 4-FIG. 11.

For example, the method of automatically generating an image report may include: obtaining a target image; obtaining a first feature image from the target image, the first feature image including an image of a region of interest in the target image; obtaining a second feature image that matches the first feature image; obtaining a knowledge graph, the knowledge graph including a relationship between the second feature image and corresponding image description information and diagnostic result information; looking up the image description information and the diagnostic result information corresponding to the second feature image based on the knowledge graph and the second feature image; and generating an image report based on the target image, the image description information, and the diagnostic result information.

In some embodiments, when the image report is automatically generated according to the image report generation method described in FIG. 4-FIG. 11, a knowledge graph may need to be constructed. An original text and an original image may be obtained during constructing the knowledge graph. The original text may be performed the error correction, and then be stored. In some embodiments, the obtained original text may be used as the text to be processed, and the obtained original text may be performed the error correction based on the text correction method described in FIG. 12-FIG. 22. The original text and the original image may be obtained from a book, a newspaper, a website, an electronic medical record, a test order, a diagnostic report, etc. The original text, the original image, and feature images may be unstructured data, and be stored based on the unstructured data storage method described in FIG. 23-FIG. 27. The feature image or the text may be retrieved from a feature image database or the knowledge graph based on the unstructured data storage method described in FIG. 23-FIG. 27.

In 2840, error detection and error correction may be performed on the image report.

In some embodiments, error detection may be performed on the image report to obtain the type and the position of an error text. A target error correction strategy corresponding to the type of the error text may be determined based on a corresponding relationship between the type of the error text and an error correction strategy. The error correction on the error text may be performed based on the target error correction strategy and the location of the error text to generate a final report. More descriptions for the error detection and the error correction of the text may be found elsewhere in the present disclosure (e.g., FIGS. 12-22 and the descriptions thereof).

In 2850, the image report may be stored.

In some embodiments, after the final report (unstructured data) is generated, structured medical data corresponding to the final report and a corresponding relationship between the formal report and the structured medical data may be obtained by analyzing the final report. The structured medical data and the corresponding relationship may be stored into a fourth database, the formal report may be stored into a fifth database.

In 2860, the image report may be retrieved.

In some embodiments, a query request may be input on the user terminal 130 by a user (e.g., a medical person). The data processing system 110 may retrieve the structured data corresponding to the input query request from the fourth database. The data processing system 110 may retrieve the corresponding unstructured data (e.g., an image report) from the fifth database based on a corresponding relationship between the unstructured data and the structured medical data. More descriptions for the obtaining, retrieving and storage of the unstructured data may be found elsewhere in the present disclosure (e.g., FIGS. 23-27 and the descriptions thereof).

It should be noted that the above description for the process 2800 is merely provided for the purposes of illustration, and not intended to limit the scope of the present disclosure. For persons having ordinary skills in the art, multiple variations and modifications of the process 2800 may be made under the teachings of the present disclosure. However, those variations and modifications do not depart from the scope of the present disclosure.

The above descriptions are related to different aspects of an imaging system and method and/or the implementing method of other operations through a program. The program in the technology may be regarded as a "product" or "article" in the form of executable code and/or related data, which is participated in or realized by a computer-readable medium. Tangible and permanent storage medium may include any memory or storage used by computers, processors, similar devices, or related modules, such as various semiconductor memories, tape drives, disk drives, or similar devices that can provide storage functions for software at any time.

All software or some of them may sometimes communicate via a network, such as an internet or other communication networks. Such communication may load software from one computer device or processor to another. For example, software may be loaded from a management server or a host computer of an imaging system to a hardware platform of a computer environment, other computer environment that implements the system, or a system with similar functions to provide information required for on-demand services. Thus, another medium capable of transmitting a software element can also be used as a physical connection between the local devices, such as an optical wave, a radio wave, an electromagnetic wave, etc., which may implement propagation via a cable, an optic cable, or the air. Physical medium used to carriers such as cables, wireless connection, or optic cables, etc., may also be considered to a medium carrying software. The usage here except to limit the tangible "storage" medium, the terms "readable medium" of a computer or machine refer to the medium involved in the execution of any instruction by a processor.

Thus, a computer readable medium may have a variety of forms including, but not limited to, a tangible storage medium, a carrier medium, or a physical transport medium. The stable storage medium may include an optical disk, a disk, and a storage system that can implement the system components described in the above figures in other computers or similar devices. Unstable storage medium may include a dynamic memory, such as a main memory of a computer platform. Tangible transmission medium may include a coaxial cable, a copper cable, and an optical fiber, including the lines inside a computer system that form a bus. The carrier transmission medium may transmit an electrical signal, an electromagnetic signal, an acoustic wave signal, or a light wave signal, which can be generated by radio frequencies or infrared data communication. The usual computer readable medium may include a hard disk, a floppy disk, a tape, any other magnetic medium; CD-ROM, DVD, DVD-ROM, any other optical medium; perforated card, any other physical storage medium containing the small hole mode; RAM, PROM, EPROM, FLASH-EPROM, any other memory tablet, or tape; a carrier for transmission of data or instructions, a cable, connection device for transmission of carrier, any other program code and/or data that can be read by a computer. Many of these forms of computer-readable medium occur as the processor executes instructions and passes one or more results.

Those skilled in the art may understand that there can be a variety of variations and improvements in the contents disclosed herein. For example, the different system components described above may be implemented by hardware devices, but may also be implemented only by software. For example, the system may be installed on an existing server. Further, the supply information disclosed herein may be implemented by a firmware, a combination of firmware/software, a combination of firmware/hardware, or a combination of hardware/firmware/software.

The above contents describe contents of the present disclosure and/or some other examples. According to the above descriptions, the present disclosure may also make different deformations. The subjects disclosed herein may be implemented in different forms and examples, and the present disclosure may be applied to many applications. All applications, modifications, and changes claimed by the claims belong to the scope of the present disclosure.

What is claimed is:

1. A system, comprising:
at least one storage device includes a set of instructions;
at least one processing device configured to communicate with the at least one storage device, wherein when executing the set of instructions, the at least one processing device is configured to direct the system to perform at least one operation including:

obtaining a target image;
obtaining a first feature image from the target image, the first feature image including a region of interest (ROI) in the target image;
obtaining a knowledge graph, the knowledge graph including a graph structure indicating an entity type and an entity connection relationship, the entity type including an image entity and a text entity, the image entity including an original image and a feature image obtained from the original image, the text entity including a description of the feature image, a diagnostic result, a disease, a treatment plan, and at least one of an incentive, a symptom, or a medicine, the entity connection relationship represents a relationship between the image entity and the text entity;
obtaining, from the knowledge graph, a second feature image that matches the first feature image;
obtaining image description information, diagnostic result information, treatment plan information, disease information, and at least one of incentive information, symptom information, or medicine information corresponding to the second feature image based on the knowledge graph and the second feature image;
generating an image report of the target image based on the target image, the image description information, the diagnostic result information, the treatment plan information, the disease information, and the at least one of the incentive information, the symptom information, or the medicine information;
obtaining a type and a location of an error text of the image report by performing an error detection on the image report of the target image, the type of the error text being determined from a type of wrong word, a type of absence, a type of disorder, or a type of redundancy;
determining a target error correction strategy corresponding to the type of the error text based on a corresponding relationship between the type of the error text and the target error correction strategy, the target error correction strategies corresponding to the type of wrong word, the type of absence, the type of disorder, and the type of redundancy being different; and
performing an error correction on the error text based on the target error correction strategy and the location of the error text.

2. The system of claim 1, wherein the knowledge graph is provided by performing operations including:
determining the graph structure of the knowledge graph;
obtaining an original text and the original image of a preset field;
extracting entity data from the original text and the original image;
determining an association relation among the entity data; and
determining the knowledge graph of the preset field based on the graph structure, the entity data, and the association relation.

3. The system of claim 2, wherein
extracting the entity data from the original text and the original image comprises:
obtaining a plurality of word segmentation results outputted by a trained word segmentation model by inputting the original text into the trained word segmentation model;

obtaining a plurality of feature texts outputted by a trained entity identification model by inputting the plurality of word segmentation results into the trained entity identification model; and determining the plurality of feature texts as the entity data; and determining the association relation among the entity data comprises:

obtaining the association relation among the plurality of feature texts by inputting the original text and the plurality of feature texts into a trained relation extraction model.

4. The system of claim 3, wherein the extracting the entity data from the original text and the original image further includes:

determining N-Gram results by performing N-Gram frequency statistics on the plurality of word segmentation results;

receiving artificial verification information for the N-Gram results;

merging one of the N-Gram results into a vocabulary according to the artificial verification information;

using the vocabulary to update a word segmentation dictionary;

updating the word segmentation model according to the updated word segmentation dictionary.

5. The system of claim 2, wherein extracting the entity data from the original text and the original image comprises:

obtaining an identification result outputted by an identification model by inputting the original image into a trained identification model, the identification result being configured to indicate a region of interest (ROI) in the original image;

obtaining the feature image of the region of interest in the original image; and determining the feature image of the original image as the entity data.

6. The system of claim 2, wherein extracting the entity data from the original text and the original image comprises:

extracting, from the original text, the image description text and the diagnostic result text corresponding to the original image;

extracting the feature image from the original image; and determining the image description text, the diagnostic result text, and the feature image of the original image as the entity data; and determining the association relation among the entity data comprises:

determining the association relation among the feature image of the original image, the image description text, and the diagnostic result text.

7. The system of claim 2, wherein determining the knowledge graph of the preset field based on the graph structure, the entity data, and the association relation among the entity data comprises:

dividing the entity data into a plurality of triads based on the association relation among the entity data; and generating the knowledge graph by filling the plurality of triads into the graph structure.

8. The system of claim 1, wherein the type of the error text includes at least one of the type of wrong word, the type of absence, or the type of disorder; and performing the error correction on the error text based on the target error correction strategy and the location of the error text comprises:

determining at least one candidate text corresponding to the error text based on the target error correction strategy and the location of the error text; and performing the error correction on the error text based on the at least one candidate text.

9. The system of claim 8, wherein the type of the error text includes the type of wrong word; and determining the at least one candidate text corresponding to the error text based on the target error correction strategy and the location of the error text comprises:

extracting a text of the type of wrong word from the image report based on a location of the text of the type of wrong word; and selecting, from a first database as the at least one candidate text, at least one of a text that is a homophone with the type of wrong word or a text having a similarity degree to the text of the type of wrong word greater than a similarity threshold.

10. The system of claim 8, wherein the type of the error text includes the type of absence; and determining the at least one candidate text corresponding to the error text based on the target error correction strategy and the location of the error text comprises:

extracting, from the image report based on a location of the text of the type of the absence, a text adjacent to a text of the type of the absence; and selecting, from a second database, a text that matches the adjacent text as the at least one candidate text.

11. The system of claim 8, wherein the type of the error text includes the type of disorder; and determining the at least one candidate text corresponding to the error text based on the target error correction strategy and the location of the error text comprises:

extracting a text of the type of disorder from the image report based on a location of the text of the type of disorder; and selecting, from a third database as the at least one candidate text, a text that includes one or more same words as the text of the type of disorder.

12. The system of claim 8, wherein performing the error correction on the error text based on the at least one candidate text comprises:

obtaining at least one added text to be processed by adding the at least one candidate text to the corresponding location of the error text;

determining a score of each of the at least one added text to be processed that indicates a fluency degree of the added text to be processed;

ranking the at least one added text to be processed in a descending order based on the score of the at least one added text to be processed, and determining the added text to be processed that has a highest score as a corrected text.

13. The system of claim 1, wherein the type of the error text includes the type of redundancy, and determining the at least one candidate text corresponding to the error text based on the target error correction strategy and the location of the error text comprises:

determining, based on the target correction strategy and the location of the error text, whether to delete a text of the type of redundancy;

in response to a determination of deleting the text of the type of redundancy, deleting the error text; or in response to a determination of not deleting the text of the type of redundancy, retaining the error text.

14. The system of claim 13, wherein determining, based on the target correction strategy and the location of the error text, whether to delete a text of the type of redundancy comprises:

extracting the text of the type of redundancy from the image report based on a location of the text of the type of redundancy;

determining whether the text of the type of redundancy is smooth by inputting the text of the type of redundancy into a trained language model;

in response to determining that the text of the type of redundancy is not smooth, deleting the text of type redundancy; or in response to determining that the text of the type of redundancy is smooth, retaining the text of type redundancy.

15. The system of claim 1, wherein the image report is unstructured medical data, and the at least one processing device is configured to direct the system to perform the at least one operation including:

obtaining, by analyzing the image report, structured medical data corresponding to the image report and a corresponding relationship between the image report and the structured medical data;

storing the structured medical data and the corresponding relationship into a fourth database; and storing the image report into a fifth database.

16. The system of claim 15, wherein obtaining the structured medical data corresponding to the image report and the corresponding relationship between the image report and the structured medical data by analyzing the image report comprises:

obtaining a corresponding analysis rule from a plurality of preset analysis rules based on an unstructured medical data type of the image report;

obtaining the structured medical data corresponding to the image report by analyzing, based on the corresponding analysis rule, the image report; and determining the corresponding relationship between the image report and the structured medical data based on a data identifier of the unstructured medical data of the image report and a data identifier of the structured medical data.

17. The system of claim 15, wherein the at least one processing device is configured to direct the system to perform the at least one operation including:

receiving a query request, the query request including a data identifier of the image report;

obtaining, based on the data identifier and the query request, the structured medical data corresponding to the data identifier by accessing the fourth database; and obtaining the image report from the fifth database based on the structured medical data corresponding to the data identifier and the corresponding relationship.

18. The system of claim 1, wherein the text entity includes the description of the feature image, the diagnostic result, the disease, the treatment plan, the incentive, the symptom, and a medicine.

19. A data processing system, comprising:

at least one storage device including a set of instructions;

at least one processing device configured to communicate with the at least one storage device, wherein when executing the set of instructions, the at least one processing device is configured to direct the system to perform operations including:

obtaining a type and a location of an error text by performing an error detection on a text to be processed, the type of the error text being determined from a type of wrong word, a type of absence, a type of disorder, or a type of redundancy;

determining a target error correction strategy corresponding to the type of the error text based on a corresponding relationship between the type of the error text and the target error correction strategy, the target error correction strategies corresponding to the type of wrong word, the type of absence, the type of disorder, and the type of redundancy being different; and performing an error correction on the error text based on the target error correction strategy and the location of the error text.

20. A system for storing unstructured data, comprising:

at least one storage device includes a set of instructions;

at least one processing device configured to communicate with the at least one storage device, wherein when executing the set of instructions, the at least one processing device is configured to direct the system to perform operations including:

obtaining unstructured medical data to be stored, the unstructured medical data being a text;

obtaining a type and a location of an error text of the text by performing an error detection on the text, the type of the error text being determined from a type of wrong word, a type of absence, a type of disorder, or a type of redundancy;

determining a target error correction strategy corresponding to the type of the error text based on a corresponding relationship between the type of the error text and the target error correction strategy, the target error correction strategies corresponding to the type of wrong word, the type of absence, the type of disorder, and the type of redundancy being different;

performing an error correction on the error text based on the target error correction strategy and the location of the error text;

obtaining structured medical data corresponding to the unstructured medical data and a corresponding relationship between the unstructured medical data and the structured medical data by analyzing the unstructured medical data;

storing the structured medical data and the corresponding relationship into a fourth database; and storing the unstructured medical data into a fifth database.

* * * * *